US008445205B2

(12) United States Patent
Brenner

(10) Patent No.: US 8,445,205 B2
(45) Date of Patent: *May 21, 2013

(54) NUCLEIC ACID ANALYSIS USING SEQUENCE TOKENS

(75) Inventor: Sydney Brenner, Ely (GB)

(73) Assignee: Population Genetics Technologies Ltd., Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/211,113

(22) Filed: Aug. 16, 2011

(65) Prior Publication Data

US 2012/0108467 A1 May 3, 2012

Related U.S. Application Data

(63) Continuation of application No. 12/428,229, filed on Apr. 22, 2009, now Pat. No. 8,021,842, which is a continuation of application No. 11/656,746, filed on Jan. 22, 2007, now Pat. No. 7,544,473.

(60) Provisional application No. 60/761,577, filed on Jan. 23, 2006.

(51) Int. Cl.
*C12Q 1/68* (2006.01)
*C07H 21/00* (2006.01)
*C07H 21/02* (2006.01)
*C07H 21/04* (2006.01)

(52) U.S. Cl.
USPC .......... 435/6.1; 536/22.1; 536/23.1; 536/24.3

(58) Field of Classification Search
USPC .................. 435/6.1; 536/22.1, 23.1, 24.3
See application file for complete search history.

(56) References Cited

U.S. PATENT DOCUMENTS

| | | | |
|---|---|---|---|
| 5,604,097 A | 2/1997 | Brenner | |
| 5,635,400 A | 6/1997 | Brenner | |
| 5,846,719 A | 12/1998 | Brenner et al. | |
| 5,858,656 A * | 1/1999 | Deugau et al. | 435/6.12 |
| 5,888,737 A | 3/1999 | DuBridge et al. | |
| 6,045,993 A * | 4/2000 | Mahony et al. | 435/5 |
| 6,051,696 A * | 4/2000 | Maertens et al. | 536/23.1 |
| 6,136,537 A | 10/2000 | Macevicz | |
| 6,897,023 B2 | 5/2005 | Fu et al. | |
| 7,157,228 B2 | 1/2007 | Hashmi et al. | |
| 7,262,030 B2 | 8/2007 | Chen | |
| 7,306,918 B2 | 12/2007 | Hashmi et al. | |
| 7,393,665 B2 * | 7/2008 | Brenner | 435/91.1 |
| 7,425,416 B2 | 9/2008 | Hashmi et al. | |
| 7,544,473 B2 * | 6/2009 | Brenner | 435/6.12 |
| 7,635,565 B2 | 12/2009 | Hashmi et al. | |
| 8,021,842 B2 * | 9/2011 | Brenner | 435/6.11 |
| 2001/0053519 A1 * | 12/2001 | Fodor et al. | 435/6 |
| 2003/0044771 A1 | 3/2003 | Anderson et al. | |
| 2007/0269870 A1 | 11/2007 | Church et al. | |
| 2010/0216125 A1 | 8/2010 | Brenner | |

FOREIGN PATENT DOCUMENTS

| | | | |
|---|---|---|---|
| WO | 9900519 | | 1/1999 |
| WO | WO2005/012573 | * | 2/2005 |
| WO | 2006086210 | | 8/2006 |

OTHER PUBLICATIONS pUC19 Map [MBI Fementas Catalog (2000) 2 of 2 pages].*
Vos et al., AFLP: a new technique for DNA fingerprinting. Nucleic Acids Research 23(21) : 4407(1995).*
Brenner et al., "In vitro cloning of complex mixtures of DNA on microbeads: physical separation of differentially expressed cDNAs" Proceedings of the National Academy of Sciences, (2000), vol. 97, (4): 1665-70.
Collins et al., "A vision for the future of genomics research" Nature, 422: 835-847 (2003).
Gerry et al., "Universal DNA microarray method for multiplex detection of low abundance point mutations" J. Mol. Biol., 292: 251-262 (1999).
Griffiths et al., "Modern genetic analysis"; W. H. Freeman and Company, (1999); Edited by Sara Tenney, Textbook ISBN 0-7167-3118-5 Text; Chapter 10; Retrieved from the internet: <URL: http://www.ncbi.nlm.nib.gov/books/bv.fcgi?rid=mga (chapter 10 Fig 10.8).
Gunderson et al., "A genome-wide scalable SNP genotyping assay using microarray technology"; Nature Genetics, 37: 549-554 (2005).
Hardenbol et al., "Highly multiplexed molecular inversion probe genotyping: over 10,000 targeted SNPs genotyped in a single tube assay"; Genome Research, 15: 269-275 (2005).
Kennedy et al., "Large-scale genotyping of complex DNA"; Nature Biotechnology, 21: 1233-1237 (2003).
Margulies et al., "Genome sequencing in microfabricated high-density picolitre reactors"; Nature, 437: 376-380 (2005).
Shoemaker et al., "Quantative phenotype analysis of yeast deletion mutants using a highly parallel molecular bar-coding strategy"; Nature Genetics, 14: 450-456 (1996).
Stephens et al., "A screen of the complete protein kinase gene family identifies diverse patterns of somatic mutations in human breast cancer" Nature Genetics, 37: 590-592 (2005).
Syvanen "Accessing genetic variation: genotyping single nucleotide polymorphisms"; Nature Reviews Genetics, 2: 930-042 (2002).
Till et al., "High-throughput discovery of rare human nucleotide polymorphisms by ecotillin"; Nucleic Acid Research, Aug. 2006, 7:34(13): e99.
Cohen, et al. Multiple rare alleles contribute to low plasma levels of HDL cholesterol. Science. Aug. 6, 2004;305 (5685):869-72.

(Continued)

*Primary Examiner* — Ethan C Whisenant
(74) *Attorney, Agent, or Firm* — James S. Keddie; Bozicevic, Field & Francis, LLP

(57) ABSTRACT

The present invention provides methods and compositions for tagging nucleic acid sequence fragments, e.g., a set of nucleic acid sequence fragments from a single genome, with one or more unique members of a collection of oligonucleotide tags, or sequence tokens, which, in turn, can be identified using a variety of readout platforms. As a general rule, a given sequence token is used once and only once in any tag sequence. In addition, the present invention also provides methods for using the sequence tokens to efficiently determine variations in nucleotide sequences in the associated nucleic acid sequence fragments.

16 Claims, 7 Drawing Sheets

OTHER PUBLICATIONS

Druley, et al. Quantification of rare allelic variants from pooled genomic DNA. Nat Methods. Apr. 2009;6(4):263-5.

Liu, et al. Detection of extremely rare alleles by bidirectional pyrophosphorolysis-activated polymerization allele-specific amplification (Bi-PAP-A): measurement of mutation load in mammalian tissues. Biotechniques. Jan. 2004;36 (1):156-66.

* cited by examiner

A.

B.

C.

D.

NUCLEIC ACID ANALYSIS USING SEQUENCE TOKENS

CROSS-REFERENCE

This application is a continuation of U.S. patent application Ser. No. 12/428,229 filed Apr. 22, 2009, now U.S. Pat. No. 8,021,842, which is a continuation of U.S. patent application Ser. No. 11/656,746 filed Jan. 22, 2007, now U.S. Pat. No. 7,544,473, which claims the benefit of U.S. Provisional Application No. 60/761,577 filed Jan. 23, 2006, each of which are incorporated herein by reference.

BACKGROUND

There is great interest in determining nucleic acid sequences and sequence differences rapidly and efficiently for addressing a host of important problems in the biomedical sciences, e.g. Collins et al, Nature, 422: 835-847 (2003); National Cancer Institute, Report of Working Group on Biomedical Technology, "Recommendation for a Human Cancer Genome Project," (February, 2005). Not only are such measurements crucial for understanding the genetic basis of inherited traits, such as disease susceptibilities, but they are also crucial for understanding the role of somatic mutations in cancer. Many techniques have been developed and successfully applied to problems in these areas, e.g. Stephens et al, Nature Genetics, 37: 590-592 (2005); Syvanen, Nature Reviews Genetics, 2: 930-942 (2002); Kennedy et al, Nature Biotechnology, 21: 1233-1237 (2003); Hardenbol et al, Genome Research, 15: 269-275 (2005); Gunderson et al, Nature Genetics, 37: 549-554 (2005); Margulies et al, Nature, 437: 376-380 (2005); and the like. However, there are still many problems, such as the rapid and efficient discovery of genetic or epigenetic variation, that are not adequately addressed by current techniques.

Among current techniques, several have employed oligonucleotide tags, or barcodes, to represent and/or convey target sequence information from known sequences, e.g. Hardenbol et al (cited above); Shoemaker et al, Nature Genetics, 14: 450-456 (1996); Gerry et al, J. Mol. Biol., 292: 251-262 (1999). The use of such reagents is advantageous because they can be selected to maximize convenience and efficiency of identification, such as by selective and specific hybridization to complementary sequences on a microarray for a parallel readout of sequence information. However, such techniques presently measure only known mutations or polymorphisms and require large-scale synthesis of probes and tags prior to application.

The availability of a convenient and efficient molecular tagging method that could be used for discovery of genetic variation and/or high-throughput DNA sequencing would extend the use of these useful reagents and lead to improvements in analytical assays in many fields, including scientific and biomedical research, medicine, and other industrial areas where genetic measurements are important.

SUMMARY OF THE INVENTION

The present invention provides methods and compositions for tagging nucleic acid sequence fragments, e.g., a set of nucleic acid sequence fragments from a single genome, with one or more unique members of a collection of oligonucleotide tags, or sequence tokens, which, in turn, can be identified using a variety of readout platforms. As a general rule, a given sequence token is used once and only once in any tag sequence. In addition, the present invention also provides methods for using the sequence tokens to efficiently determine variations in nucleotide sequences in the associated nucleic acid sequence fragments.

The present invention provides a method of tagging a plurality of populations of polynucleotides each with a unique sequence token by generating a plurality of unique sequence token tags; dividing polynucleotides of each population into at least two non-overlapping nucleic acid segments; and ligating a unique sequence token tag to each non-overlapping nucleic acid segment of each population of polynucleotides to provide a plurality of populations of polynucleotides each tagged with a unique sequence token tag, wherein each unique sequence token tag is used to tag only one population of polynucleotides.

In some embodiments, the predetermined number of the non-overlapping segments is all non-overlapping segments of the polynucleotide. In some embodiments, each of the non-overlapping segments has a length that is the same for all such segments. In some embodiments, each population of polynucleotides includes genomic DNA from a single subject, such as a human. In some embodiments, the dividing is by restriction enzyme digestion of the polynucleotides.

The present invention also provides a method of tagging a plurality of genomic DNA samples from a plurality of subjects each with a unique sequence token by generating a plurality of unique sequence token tags; dividing each genomic DNA sample from each subjects into at least two non-overlapping nucleic acid segments; and ligating a unique sequence token tag to each non-overlapping nucleic acid segment of each genomic DNA sample to provide a plurality of genomic DNA samples from a plurality of subjects each tagged with a unique sequence token tag, wherein each unique sequence token tag is used to tag only the genomic DNA from one subject.

In some embodiments, the predetermined number of the non-overlapping segments is all non-overlapping segments of the polynucleotide. In some embodiments, each of the non-overlapping segments has a length that is the same for all such segments. In some embodiments, the subject is a human. In some embodiments, the dividing is by restriction enzyme digestion of the polynucleotides.

The present invention also provides a method of screening for the presence or absence of a rare nucleotide allele of a polymorphism in a population of enriched genomic DNA segments from a population of genomic DNA samples, by incubating a reaction mixture under polymerization conditions, including: an enriched population of non-overlapping genomic DNA segments, wherein each genomic DNA segment comprises a unique sequence token, an oligonucleotide probe complementary to a region of the genomic DNA segment upstream of a polymorphism, wherein the polymorphism comprises a rare nucleotide allele and a frequent nucleotide allele, and dideoxy nucleotide triphosphate corresponding to the rare nucleotide allele and the frequent nucleotide allele, wherein the nucleotide triphosphate corresponding to the rare nucleotide allele is conjugated to a first member of a binding pair; dividing the reaction mixture into at least two groups by exposing the reaction mixture to the second member of the binding pair to provide a first group comprising oligonucleotide probes having the nucleotide triphosphate corresponding to the rare nucleotide hybridized to the genomic DNA segments to provide a group of bound genomic DNA segments; and determining the unique sequence tokens of the bound genomic DNA segments to identify genomic DNA samples having the rare nucleotide allele of the polymorphism.

In some embodiments, the predetermined number of the non-overlapping segments is all non-overlapping segments of the polynucleotide. In some embodiments, the first binding member is biotin, avidin, strepavidin, or a magnetic bead. In some embodiments, the second binding member is biotin, avidin, strepavidin, or a magnetic bead. In some embodiments, the step of determining includes specifically hybridizing said generated sequence tokens with complements thereof attached to one or more solid phase supports. In some embodiments, the step of determining includes sequencing the sequence token or a portion thereof.

The present invention also provides a sieving device, including: at least one substrate support having an bottom surface and a top surface, wherein the bottom surface comprises a plurality linear elements and wherein each linear element comprises a unique oligonucleotide immobilized thereon; and a receiving unit having top surface comprising a microfluidic channel, wherein the bottom surface of the substrate is positioned on the top surface of the receiving unit and the linear elements of the substrate extend into the microfluidic channel. In some embodiments, the device further includes a plurality of substrate supports.

The present invention also includes a kit including: a sieving device comprising at least one substrate having a top surface and a bottom surface, wherein the bottom surface comprises a plurality linear elements and wherein each linear element comprises a unique oligonucleotide immobilized thereon, and a receiving unit having top surface comprising a microfluidic channel, wherein the bottom surface of the substrate is positioned on the top surface of the receiving unit and the linear elements of the substrate extend into the microfluidic channel; and instructions for using the sieving device to identify sequence tokens in a population. In some embodiments, the kit further includes a plurality of substrate supports.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DEFINITIONS

Figure 1A:
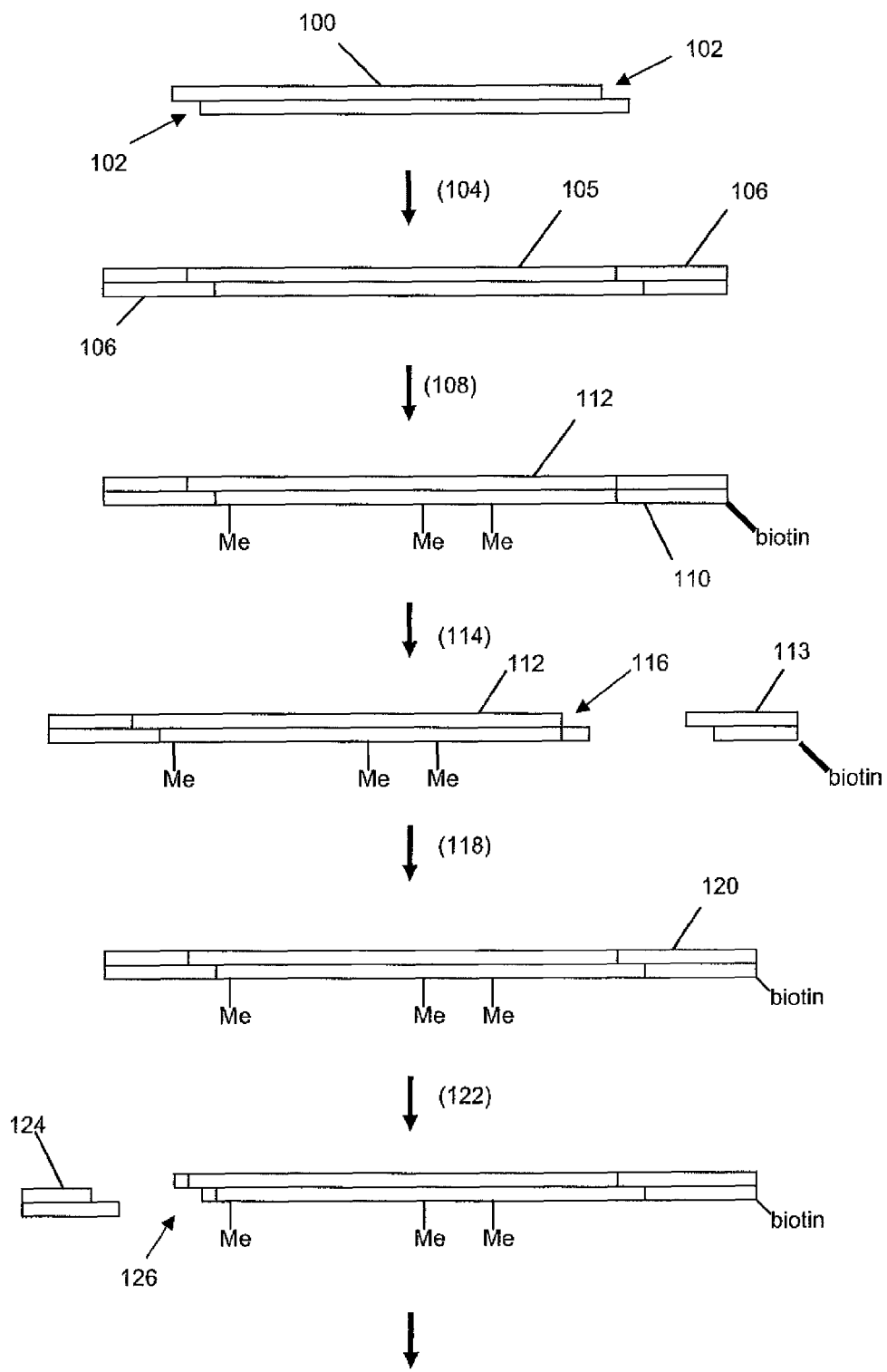
FIGS. 1A-1B illustrate a general procedure for attaching an oligonucleotide tag to one end of a polynucleotide.

Unless otherwise defined, all technical and scientific terms used herein have the same meaning as commonly understood by one of ordinary skill in the art to which this invention belongs. Still, certain elements are defined for the sake of clarity and ease of reference.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Addressable" in reference to tag complements means that the nucleotide sequence, or perhaps other physical or chemical characteristics, of an end-attached probe, such as a tag complement, can be determined from its address, i.e. a one-to-one correspondence between the sequence or other property of the end-attached probe and a spatial location on, or characteristic of, the solid phase support to which it is attached. Preferably, an address of a tag complement is a spatial location, e.g. the planar coordinates of a particular region containing copies of the end-attached probe. However, end-attached probes may be addressed in other ways too, e.g. by microparticle size, shape, color, frequency of micro-transponder, or the like, e.g. Chandler et al, PCT publication WO 97/14028.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683, 195; 4,965,188; 4,683,202; 4,800,159 (PCR); Gelfand et al, U.S. Pat. No. 5,210,015 (real-time PCR with "TAQMAN™" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

"Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Genetic locus," or "locus" in reference to a genome or target polynucleotide, means a contiguous subregion or segment of the genome or target polynucleotide. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length.

"Genetic variant" means a substitution, inversion, insertion, or deletion of one or more nucleotides at genetic locus, or a translocation of DNA from one genetic locus to another genetic locus. In one aspect, genetic variant means an alternative nucleotide sequence at a genetic locus that may be present in a population of individuals and that includes nucleotide substitutions, insertions, and deletions with respect to other members of the population. In another aspect, insertions or deletions at a genetic locus comprises the addition or the absence of from 1 to 10 nucleotides at such locus, in comparison with the same locus in another individual of a population.

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476, 930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Microarray" refers to a solid phase support having a planar surface, which carries an array of nucleic acids, each member of the array comprising identical copies of an oligonucleotide or polynucleotide immobilized to a spatially defined region or site, which does not overlap with those of other members of the array; that is, the regions or sites are spatially discrete. Spatially defined hybridization sites may additionally be "addressable" in that its location and the identity of its immobilized oligonucleotide are known or predetermined, for example, prior to its use. Typically, the oligonucleotides or polynucleotides are single stranded and are covalently attached to the solid phase support, usually by a 5'-end or a 3'-end. The density of non-overlapping regions containing nucleic acids in a microarray is typically greater than 100 per $cm^2$, and more preferably, greater than 1000 per $cm^2$. Microarray technology is reviewed in the following references: Schena, Editor, Microarrays: A Practical Approach (IRL Press, Oxford, 2000); Southern, Current Opin. Chem. Biol., 2: 404-410 (1998); Nature Genetics Supplement, 21: 1-60 (1999). As used herein, "random microarray" refers to a microarray whose spatially discrete regions of oligonucleotides or polynucleotides are not spatially addressed. That is, the identity of the attached oligonucleoties or polynucleotides is not discernable, at least initially, from its location. In one aspect, random microarrays are planar arrays of microbeads wherein each microbead has attached a single kind of hybridization tag complement, such as from a minimally cross-hybridizing set of oligonucleotides. Arrays of microbeads may be formed in a variety of ways, e.g. Brenner et al, Nature Biotechnology, 18: 630-634 (2000); Tulley et al, U.S. Pat. No. 6,133,043; Stuelpnagel et al, U.S. Pat. No. 6,396,995; Chee et al, U.S. Pat. No. 6,544,732; and the like. Likewise, after formation, microbeads, or oligonucleotides thereof, in a random array may be identified in a variety of ways, including by optical labels, e.g. fluorescent dye ratios or quantum dots, shape, sequence analysis, or the like.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structural Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 mL, to a few hundred µL, e.g. 200 µL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified.

"Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

As used herein, the term "$T_m$" is used in reference to the "melting temperature." The melting temperature is the temperature at which a population of double-stranded nucleic acid molecules becomes half dissociated into single strands.

Several equations for calculating the Tm of nucleic acids are well known in the art. As indicated by standard references, a simple estimate of the Tm value may be calculated by the equation. Tm=81.5+0.41 (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of Tm.

"Sample" means a quantity of material from a biological, environmental, medical, or patient source in which detection, measurement, or labeling of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION OF THE INVENTION

The present invention provides methods and compositions for tagging nucleic acid sequence fragments, e.g., a set of nucleic acid sequence fragments from a single genome, with one or more unique members of a collection of oligonucleotide tags, or sequence tokens, which, in turn, can be identified using a variety of readout platforms. As a general rule, a given sequence token is used once and only once in any tag sequence. In addition, the present invention also provides methods for using the sequence tokens to efficiently determine variations in nucleotide sequences in the associated nucleic acid sequence fragments.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) Biochemistry (4th Ed.) Freeman, New York, Gait, "*Oligonucleotide Synthesis: A Practical Approach*" 1984, IRL Press, London, Nelson and Cox (2000), Lehninger, *Principles of Biochemistry* $3^{rd}$ Ed., W.H. Freeman Pub., New York, N.Y. and Berg et al. (2002) *Biochemistry*, $5^{th}$ Ed. W.H. Freeman Pub., New York, N.Y., all of which are herein incorporated in their entirety by reference for all purposes.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Overview

In general, the present invention provides sequence tokens that can be used as markers for use in tagging nucleic acid sequences to allow for high throughput screening of the associated nucleic acid sequences and to enable identification of the source of any particular nucleic acids of interest. A set of sequence tokens is generally designed so that each sequence token within the set has a unique sequence that is different than the other sequence tokens in the set and does not cross-hybridize with the other sequence tokens in the set. Therefore, based on the uniqueness of the sequence, each sequence token can be detected independently of all the other sequence tokens in the set by a unique probe. Similar to any other oligonucleotide sequence, a sequence token or a concatenation of two or more sequence tokens can be ligated to DNA and can be used as a unique identification and sorting tag for the particular associated DNA.

As described in greater detail below, the present invention is based on the principle that a single unique sequence token is used only once to tag a subgroup of a population of nucleic acid sequences. For example, if a population of nucleic acids includes 12 subgroups, 12 different sequence tokens would be needed so that each subgroup of nucleic acids is tagged with a different sequence token. In some embodiments, a population of nucleic acids will include a mixture of genomic DNA from a population of samples (e.g., cell lines) or subjects, such as human subjects. In such embodiments, all genomic DNA from a first sample or subject is tagged with a first unique sequence token and all the genomic DNA from a second sample or subject is tagged with a second unique sequence token.

In such embodiments, all genomic DNA from a first sample or subject can be digested into approximately 1 kilobase (kb) fragments and to all nucleic acid fragments from the first individual a first unique sequence token can be ligated as described below while all genomic DNA of a second sample of subject can digested into approximately 1 kb fragments and to and to all nucleic acid fragments from the second individual a second unique sequence token can be ligated. This process can be repeated for genomic DNA from a whole population of samples or subject.

As a result of the tagging process, the genomic DNA fragments from each sample or subject in the population would be tagged with a unique sequence token such that the particular sequence token used for any one sample or subject is not used for any other sample or subject in the population. Therefore, once all the genomic DNA fragments from the samples or subjects in the population are tagged with sequence tokens, the collection of tagged nucleic acids can be pooled and analyzed. The pooled nucleic acids can subsequently be sorted based on the unique sequence tokens. In addition, based on the uniqueness of the sequence token tags, any one tagged nucleic acid fragment can be identified as belonging to any one original sample or subject based on the unique sequence token tag used to tag all the genomic DNA fragments of the particular sample or subject.

Like any other nucleic acid sequence, a sequence token can be added by ligation to DNA and can be used as a unique tag, or as part of a unique tag. However, unlike conventional combinatorial tags, e.g. Brenner et al, Proc. Natl. Acad. Sci., 97: 1665-1670 (2000), where the position of an elementary unit is important, in the present invention the location of addition of a sequence token does not matter. For example, in a selection or generation process in accordance with the present invention, the sequence tokens can be grouped or added in any order, anywhere, even in branched structures. In an exemplary process described below, it is only a matter of convenience that the sequence tokens are affixed to the sample in a sequential manner and that their order may reflect the original sample identity of the tagged polynucleotide being analyzed within a larger tagged population of sample.

Sequence tokens can be used to label a sample at one particular position within the sample or at multiple positions. Multiple positions are useful in order to enable larger numbers of samples to be labeled more efficiently. The number of particular labeling positions can be defined at the 'base' of such labeling. Each of the possible positions could be labeled by any one of a unique set of tokens and the tokens for any one such set are different from those tokens that comprise each of the other sets. The number of tokens in each set can be defined as the 'dimensionality' of the process. Thus, if one had 32 unique sequence tokens divided into 4 sets corresponding to 4 possible labeling positions, the base of such labeling would be 4 and the dimensionality would be 8 (which is 32 divided by 4). The number of unique sequence tokens required to tag a population of individual DNAs depends on the integer value of the base and the integer value of the dimensionality as shown below for tagging 4,096 individual genomes:

| Base | Dimensionality | No. of Seq. Tokens |
| --- | --- | --- |
| 2 | 12 | 24 |
| 4 | 6 | 24 |
| 8 | 4 | 32 |
| 16 | 3 | 48 |
| 64 | 2 | 128 |
| 4,096 | 1 | 4,096 |

In general, the present system provides compositions and methods for tracking and identifying all DNA from a particular sample or subject in a mixed population. The system allows for parallel analysis of DNA from a whole population and the capability of specifically identifying which individuals carry a particular genetic variation of interest. As such, the system is particularly useful for identifying genetic variations at particular locations in genomic DNA of a population of individuals and for identifying the presence of any rare alleles as well as carriers of the rare alleles as described in greater detail below.

The following description provides guidance for making and using the compositions of the invention, and for carrying out the methods of the invention.

Constructing of a Set of Mutually Discriminatory Sequence Tokens

In one aspect, sequence tokens of the invention are designed so that there are no adjacent GC pairs. In general, the sequence tokens are generated from a set of units called "triplets." Each triplet group has four members, wherein each member of the group is different from the other members by at least 2 out of 3 bases. Each triplet group has what is referred to as a "dual" group, wherein every member of the dual group differs from the original triplet group by at least 1 out of 3 bases. The properties of the dual triplets are the same as the original set. This has the effect that when a sequence composed out of one form is defined, then its dual can immediately be included.

Triplets and methods for constructing sequence tokens from triplets are described below. Sequences are designed to be as different as possible from one another, i.e. mutually discriminatory, to ensure hybridization occurs or ensure that hybridization does not occur. The triplets are defined as "$s_i w_j$," where s is G or C, w is A or T, and i and j are either 0 or a positive integer and represent, respectively, the number of s elements or w elements present in the triplet. The dual of any triplet is characterized by appending an apostrophe, as exemplified below:

TABLE 1

Exemplary Triplet and Corresponding Dual Groups

| Triplet | | Dual |
|---|---|---|
| 1. | sww | sww' |
| | CAA | CAT |
| | GAT | GAA |
| | CTT | CTA |
| | GTA | GTT |
| 2. | wsw | wsw' |
| | TGA | TGT |
| | AGT | AGA |
| | TCT | TCA |
| | ACA | ACT |
| 3. | wws | wws' |
| | TAG | TAC |
| | AAC | AAG |
| | TTC | TTG |
| | ATG | ATC |
| 4. | www | www' |
| | TAA | TAT |
| | AAT | AAA |
| | TTT | TTA |
| | ATA | ATT |
| 5. | sws | sws |
| | CAG | CAC |
| | GAC | CAG |
| | CTC | CTG |
| | GTG | GTC |

The above exemplary triplets can be classified as either symmetric or asymmetric. For example, in symmetric triplets, such as wsw, www, and sws, the duals are the inverse complements of the corresponding triplets, that is, sws and sws' are complementary to each other in the sense that each member of sws has a complement in the set sws'. In asymmetric triplets, sww and wws, sequences have been chosen such that sww and wws' are complementary as are sww' and wws'.

As mentioned above, the differences between the members of the triplets are designated in table 2 below as "<3>" for 3 out of 3 being different, "<2>" for at least 2 out of 3 being different, or "<1>" for at least 1 out of 3 being different.

TABLE 2

Base Differences Between Triplet Groups

| | sww | wsw | wws | www | sws |
|---|---|---|---|---|---|
| sww | <2> | | | | |
| wsw | <2> | <2> | | | |
| wws | <2> | <2> | <2> | | |
| www | <1> | <1> | <1> | <2> | |
| sws | <1> | <3> | <1> | <2> | <2> |

From these triplets, a set of exemplary 9-base sequence tokens is chosen so that each member of the set has the same base composition $w_6s_3$ (i.e., each sequence token includes 3 s elements and 6 w elements) with no ss conjunctions. Each 9-base sequence token is referred to herein as a "trio" as it is composed of three triplets. By "the same base composition" is meant that all the sequence tokens have the same number of s elements and w elements, where s is G or C and w is A or T.

TABLE 3

Exemplary Set of Nine-base Sequence Tokens sws.wsw.www sww.sww.wsw sww.wsw.wsw wws.wsw.wws wws.wws.wsw sws.wws.www sww.sww.wws sww.wsw.wws sww.wws.wsw wws.wws.wws sws.www.sww wsw.sws.www wsw.wsw.sww sww.wws.wws wws.www.sws sws.www.wsw wsw.sww.sww wsw.wsw.wsw sww.www.sws www.sws.wsw sws.www.wws wsw.sww.wsw wsw.wsw.wws wsw.wws.wsw www.sws.wws sww.sws.www wsw.sww.wws wws.wsw.sww wsw.wws.wws www.sww.sws sww.sww.sww sww.wsw.sww wws.wsw.wsw wsw.www.sws www.wsw.sws An exemplary set of thirty-five different trios are shown in Table 3. Concern about complementary sequences being included in the above set is unnecessary, because triplets have already been selected to avoid this. Thus, the components of sww triplet group (CAA, GAT, CTT, GTA) are not complementary to the components of wws triplet group (CAA, GAT, CTT, GTA). The components that are complementary to the sww triplet group are found in the wws' dual group.

There are four representations for each triplet and, therefore, for any 9-base sequence token there are 4×4×4 (=64) potential sequences. Of the 64 different potential sequences, each specific sequence differs from the other 63 sequences by at least two out of the nine bases. In the exemplary set of 9-base sequence tokens of Table 3, there are 35 different trio sets, which means that there are 2,240 different 9-base sequences differing from each other by at least 2 out of 9 bases. The corresponding dual groups can be added and provisions can be made for symmetry breaking, such as adding an "A" to each of the 9-base sequence tokens. This would give a total of 4,480 exemplary sequence tokens with high discrimination, 20%, which can be used as ligation codes.

A smaller subset of sequence tokens can also be selected such that each member differs from the other members by at least 4 out of the 9 bases. Such a selection can be made by examining the individual trios to select the subset which fits the requirement. The structure resembles that of the genetic code, and of the 64 sequences in each trio, a set is chosen, such that each trio has only one triplet in common with all the others. If the members of each triplet group are re-named as a, b, c, and d (for example, the members of triplet group sww could be "a" for CAA, "b" for GAT, "c" for CTT, and "d" for GTA), equivalent to A, G, C, and T in the code, then a subset obeying the rules is the following:

| I. | aaa abb acc add |
|---|---|
| | bab bbc bcd bda |
| | cac cbd cca cdb |
| | dad dba dcb ddc |

There are four other exemplary ways to generate this subset, the other three being as follows:

```
II.      baa  bbb  bcc  bdd
         cab  cbc  ccd  cda
         dac  dbd  dca  ddb
         aad  aba  acb  adc
III.     caa  cbb  ccc  cdd
         dab  dbc  dcd  dda
         aac  abd  aca  adb
         bad  bba  bcb  bdc
IV.      daa  dbb  dcc  ddd
         aab  abc  acd  ada
         bac  bbd  bca  bdb
         cad  cba  ccb  cdc
```

Within each set, the trios differ from each other by 4 out of the 9 bases; between sets the differences are 2 out of the 9 bases. As will be described, there are advantages in using different subsets, particularly to remove or minimize instances of complementary interactions between sequence tokens.

To give an example, consider the trio sequence "wws.wsw.sww". The inverse complement of this sequence is a member of the same trio. The transform can be written:

```
→
wws.wsw.sww        →        wws.   wsw.   sww
(wws.wsw.sww)'              (wws)' (wsw)' (sww)'
     ←
```

The inverse complement of a particular trio comprised of triplets is trio of the corresponding duals. Define the following representations.

| wws | sww' | sww | wws' | wsw | wsw' |
|-----|------|-----|------|-----|------|
| a AAC | GTT a' | a CTT | AAG a' | a ACA | TGT a' |
| b ATG | CAT b' | b GAT | ATC b' | b AGT | ACT b' |
| c TAG | CTA c' | c GTA | TAC c' | c TCT | AGA c' |
| d TTC | GAA d' | d CAA | TTG d' | d TGA | ACT d' |

The above are normal representations and their assigned inverse complements, transforming x→x' in the dual. A type I selection for the normal representation is chosen and the particular trio "bcd" (wws.wsw.sww), which is defined below, is considered.

```
      →
    b   c   d
   ATG TCT CAA
```

The inverse complement, written below, is:

```
      →
    b   c   d
   ATG TCT CAA

TAC AGA GTT
    b'  c'  d'
       ←
```

This follows the rule that the inverse complement of bcd, (bcd)'=d'e' b'=(dcb)'. It is noted that (dcb) is included in a type I arrangement, but is not present in any of the other three types. Therefore, a type II representation for the dual is chosen in which the perfect match is not found. There are three sequences which match to some extent:

```
     →
   bcd           ATG TCT CAA a'c'd'        TTG AGA GTT
     ← b'd'd'        TAC TCA GTT
     ← b'c'a'        TAC AGA GAA
     ←
```

These, the closest approximations, each contain two base mismatches and the underlined triplets show wherein the mismatches occur in the inverse complements. Shown below are the different approximations for bcd in the four types preserving the doublet c'd'←

```
              →
   I    bcd           ATG TCT CAA

I    b'c'd'        TAC AGA GTT
          ←

II   a'c'd'        TTG AGA GTT
          ←

III  d'c'd'        AAG AGA GTT
          ←

IV   c'c'd'        ATC AGA GTT
          ←
```

Two mismatches in nine bases are introduced in the duals chosen in this way, which, as shown below, can be additionally enhanced.

The discussion above shows that 16 representations can be chosen for each trio which differs from the other trios in the group by 4 out of 9 bases. Furthermore, the same can be done for the dual representation and sets of 16 can be chosen in such a way that the duals do not contain perfectly matched sequences complementary to the trios tokens. As seen later, the two sets may therefore be used together. Now, a subset is selected from the set of 35 trios that will have the maximum distance of 4 mismatches out of 9 bases.

Below are represented the trio sequences recording only the positions of the s residues. A set of 9 trios can be selected that differ from each other in at least two out of the three positions of the s residues. As exemplified below, token numbers 1, 3, and 7, each have an s at position 3, but are different with respect to the two other position at which the s is present. For example, token number 1 has an s at positions 1, 3, and 6, while token number 7 has an s present at positions 3, 7, and 9. The neighbors differ in three positions, and appear on a diagonal. The number of mismatches is twice the position differences (2×2=4); thus these exemplary trios will differ in 4 out of the 9 bases, as can be seen from the sequences shown side by side below (A=sww, B=wsw, C=wws, D=www, and E=sws):

| Token number | s residue positions | Full sequence representation | Triplet representation |
|---|---|---|---|
| 1 | 1 3 6 | sws.wws.www | ECD |
| 2 | 2 4 7 | wsw.sww.sww | BAA |
| 3 | 3 5 8 | wws.wsw.wsw | CBB |
| 4 | 4 6 9 | www.sws.wws | DEC |
| 5 | 1 5 7 | sww.wsw.sww | ABA |
| 6 | 2 6 8 | wsw.wws.wsw | BCB |
| 7 | 3 7 9 | wws.www.sws | CDE |
| 8 | 1 4 8 | sww.sww.wsw | AAB |
| 9 | 2 5 9 | wsw.wsw.wws | BBC |

Within each of the nine trios a set of 16 representations can be assigned, which differ from each other in 4 out of the 9 bases. Therefore, 9×16 (=144) 9-base sequence tokens can be selected with this property. An equivalent set can be selected from the dual group representations. These differ from the normal representations in one base out of three in each triplet and differ from the normal set in 3 out of the 9 based. Since the duals contain sequences complementary to the triplets, the complementarity can be minimized, as shown above, by selection of the appropriate subset. Moreover, an extra base can be added to the right hand end, A in the case of the triplet (normal) representations, and T in the case of the dual representations. This additional nucleotide breaks the symmetry even further but also adds a base difference. A total of 288 10-base sequence tokens can be defined in two sets of 144. Within each set the tokens differ by at least 4 out of 10 bases from each other (a discrimination of 40%). The two sets also differ from each other in 4 out of 10 bases, and may be used together.

The system can be extended to larger sequences with the preservation of orthogonality. These are referred to as "quartets" and can be seen below as an "s position" representation:

| s residue positions | | | | Triplet representation |
|---|---|---|---|---|
| 1 3 6 | | 12a | | ECDCa |
| 2 4 7 | | 12a | | BAACa |
| 3 5 8 | 11 | a | | CBBBa |
| 4 6 9 | 11 | a | | DECBa |
| 1 5 7 | 10 | a | | ABAAa |
| 2 6 8 | 10 | a | | BCBAa |
| 3 7 9 | | g | | CDEDg |
| 1 4 8 | | g | | AABDg |
| 2 5 9 | | | | |

Note that only 4 of the five triplets, A, B, C, and D, are used (A=sww, B=wsw, C=wws, D=www) and that a "g" is added to the last two and an "a" is added to the rest to provide the correct base composition, since D is www. A set of 128 quartet sequences can be defined, differing in 6 out of 13 bases from each other. A further 128 may be chosen from the duals: these also differ in 6 out of 13 bases from each other and if a "t" is added instead of an "a" and "c" instead of "g," then a difference of 5 out of 13 bases is defined between the two sets. Choosing the quartet representation is an extension of the triplets. On of the choices is as follows:

aaaa abbd accc addb babb bbca bcdd bdac cacc cbdb ccaa cdbd dadd dbac dcbb ddca

Quintuplets can be built up in the same way as above. Using the letter designation of the triplets, it is noted that the differences between adjacent trios are 6 out of 9 bases, and 4 out of 9 bases elsewhere.

| | ECD | BAA | CBB | DEC | ABA | BCB | CDE | AAB | BBC |
|---|---|---|---|---|---|---|---|---|---|
| ECD | — | | | | | | | | |
| BAA | 6 | — | | | | | | | |
| CBB | 4 | 6 | — | | | | | | |
| DEC | 4 | 4 | 6 | — | | | | | |
| ABA | 4 | 4 | 4 | 6 | — | | | | |
| BCB | 4 | 4 | 4 | 4 | 6 | — | | | |
| CDE | 4 | 4 | 4 | 4 | 4 | 6 | — | | |
| AAB | 4 | 4 | 4 | 4 | 4 | 4 | 6 | — | |
| BBC | 6 | 4 | 4 | 4 | 4 | 4 | 4 | 6 | — |

To achieve quartets with 8 differences between each member out of 15, duos must be added that have the same property, a difference of 2 out of 6 bases for adjacent duos, and 4 out of 6 bases elsewhere. This can be done in two ways but only 5 duos can be shown to obey the rule as shown below:

| | AA | AC | BC | BB | CB | | | AA | AB | BB | BC | CC |
|---|---|---|---|---|---|---|---|---|---|---|---|---|
| AA | — | | | | | | AA | — | | | | |
| AC | 2 | — | | | | | AB | 2 | — | | | |
| BC | 4 | 2 | — | | | | BB | 4 | 2 | — | | |
| BB | 4 | 4 | 2 | — | | | BC | 4 | 4 | 2 | — | |
| CB | 4 | 4 | 4 | 2 | — | | CC | 4 | 4 | 4 | 2 | — |
| AB | 2 | 2 | 4 | 2 | 2 | | BA | 2 | 4 | 2 | 2 | 4 |
| ED | 2 | 2 | 4 | 4 | 2 | | DE | 2 | 4 | 4 | 2 | 2 |
| BA | 2 | 4 | 2 | 2 | 4 | | ED | 2 | 2 | 4 | 4 | 2 |
| DE | 2 | 2 | 2 | 4 | 4 | | CB | 4 | 2 | 2 | 4 | 2 |
| CC | 4 | 2 | 4 | 2 | 2 | | AC | 2 | 2 | 4 | 2 | 2 |

The tables show the matches of the residual duos to the selected sets.

In each case, residual duos can be arranged into a set of four obeying the same rule:

|    | AB | ED | BA | DE |    | BA | DE | ED | CB |
|----|----|----|----|----|----|----|----|----|----|
| AB | —  |    |    |    |    | BA | —  |    |    |
| ED | 2  | —  |    |    |    | DE | 2  | —  |    |
| BA | 4  | 4  | —  |    |    | ED | 4  | 4  | —  |
| DE | 4  | 4  | 2  | —  |    | CB | 4  | 4  | 2  | — |
| CC | 4  | 2  | 4  | 2  |    | AC | 4  | 2  | 2  | 4 |

Thus, two subsets of sequence tokens can be created, one with five quartets, the other with 4 using either subset. There are 80 in the first, and 64 in the second. Each member of each subset will differ from other members by 8 out of 15 bases; between the subsets, the minimum difference is 6 out of 15. The quintets can be arranged to give 16 sets differing between each member in 8 of 15 bases. By the appropriate choice of dual representations, the differences between subsets can be increased to 8 of 15. Thus, at least 144 sequence tokens are available with differences amounting to 8 out of 15.

Attaching Sequence Token Tags to Polynucleotides

Figure 1B:
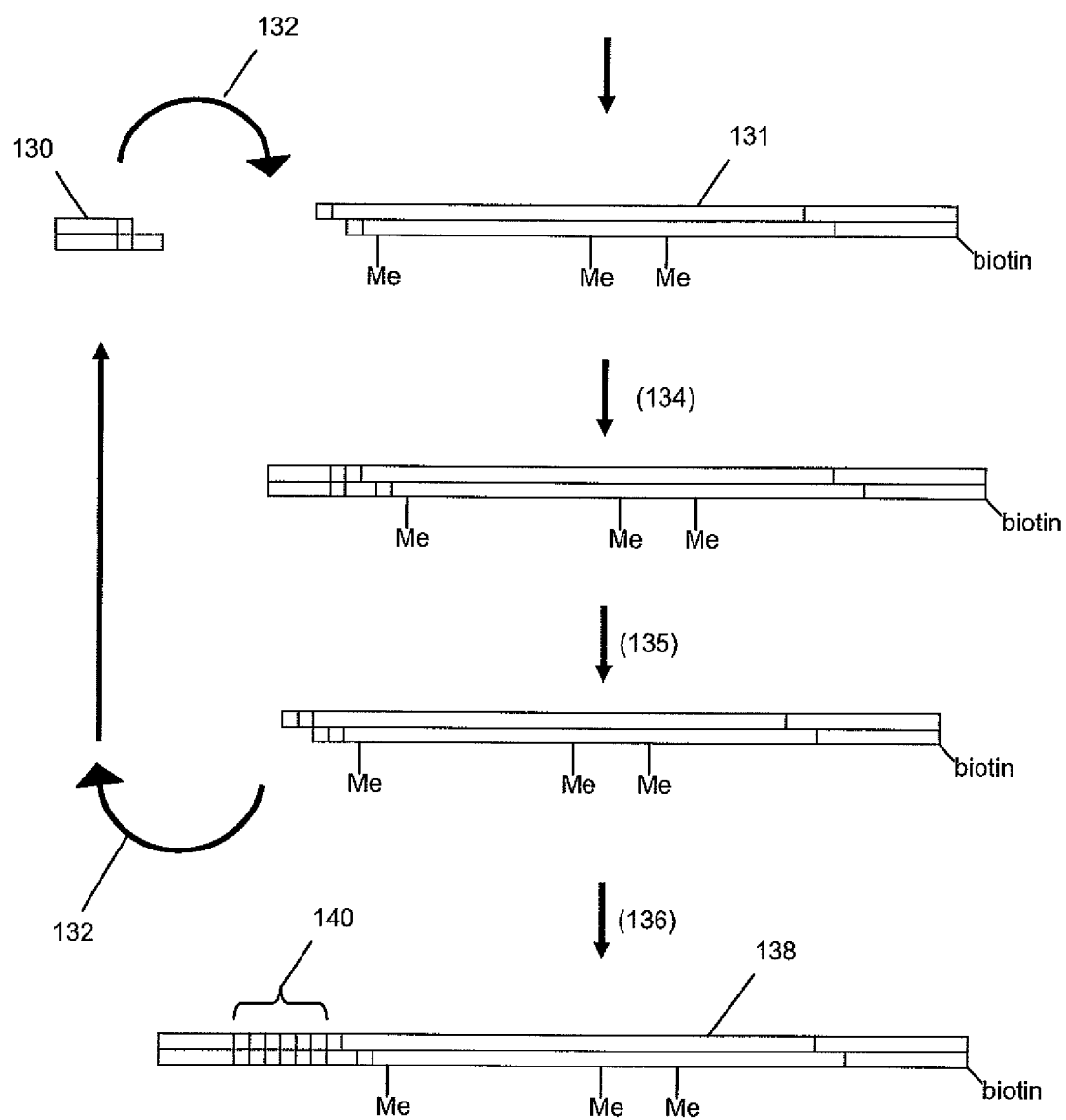

A general procedure for attaching oligonucleotide tags of the invention to polynucleotides is illustrated in FIGS. 1A-1B. Polynucleotides (100) are generated that have overhanging ends (102), for example, by digesting a sample, such as genomic DNA, cDNA, or the like, with a restriction endonuclease. Preferably, a restriction endonuclease is used that leaves a four-base 5' overhang that can be filled-in by one nucleotide to render the fragments incapable of self-ligation. For example, digestion with Bgl II followed by an extension with a DNA polymerase in the presence of dGTP produces such ends. Next, to such fragments, initial adaptors (106) are ligated (104). Initial adaptors (106) (i) attach a first segment, or word, of an oligonucleotide tag to both ends of each fragment (100). Initial adaptors (106) also contain a recognition site for a type IIs restriction endonuclease that preferably leaves a 5' four base overhang and that is positioned so that its cleavage site corresponds to the position of the newly added segment. (Such cleavage allows segments to be added one-by-one by use of a set of adaptor mixtures containing pairs of segments, or words). In one aspect, initial adaptor (106) is separately ligated to fragments (100) from each different sample, e.g. each different individual genome within a population.

In order to carry out enzymatic operations at only one end of adaptored fragments (105), one of the two ends of each fragment is protected by methylation and operations are carried out with enzymes sensitive to 5-methyldeoxycytidine in their recognition sites. Adaptored fragments (105) are melted (108) after which primer (110) is annealed as shown and extended by a DNA polymerase in the presence of 5-methyldeoxycytidine triphosphate and the other dNTPs to give hemi-methylated polynucleotide (112). Preferably, primer (110) has a capture moiety attached, such as biotin, or the like. Polynucleotides (112) are then digested with a restriction endonuclease that is blocked by a methylated recognition site, e.g. Dpn II (which cleaves at a recognition site internal to the BglII site and leaves the same overhang). Accordingly, such restriction endonucleases must have a deoxycytidine in its recognition sequence and leave an overhanging end to facilitate the subsequent ligation of adaptors. Digestion leaves fragment (112) with overhang (116) at only one end and free biotinylated fragments (113). After removal (118) of biotinylated fragments (113) (for example by affinity capture with beads having avidin molecules immobilized thereon), adaptor (120) may be ligated to fragment (112) in order to introduce sequence elements, such as primer binding sites, for an analytical operation, such as sequencing, SNP detection, or the like. Such adaptor is conveniently labeled with a capture moiety, such as biotin, for capture onto a solid phase support so that repeated cycles of ligation, cleavage, and washing can be implemented for attaching segments of the oligonucleotide tags. After ligation of adaptor (120), a portion of initial adaptor (124) is cleaved so that overhang (126) is created that includes all (or substantially all) of the segment added by adaptor (106). After washing to remove fragment (124), a plurality of cycles (132) are carried out in which adaptors (130) containing pairs of segments, or individual sequence tokens, such as a triplet described above, are successively ligated (134) to fragment (131) and cleaved (135) to leave an additional segment, or sequence token to produce. Such cycles are continued until the oligonucleotide tag (140) having a concatenated sequence of individual sequence tokens are complete, after which the tagged polynucleotides may be subjected to analysis directly, or single strands thereof may be melted from the solid phase support for analysis.

In certain embodiments, it is desirable to generate concatenated sequence tokens comprising of two or more sequence tokens. This is particularly desirable in embodiments in which the concatenated sequence tokens will be used as primer sequences for PCR or sequencing. In such embodiments, the concatenated sequence tokens will have two unique sequence tokens, with the two unit concatenated sequence token being referred to as a ditoken. Each unique sequence token of the ditoken will include 9 nucleotides with the ditoken having a total of 18 nucleotides. For example, the tokens of the Group I can be concatenated with the tokens of Group II to provide a set of 32 ditokens that are capable of acting as hybridization sequences for PCR primers.

```
I.     aaa  abb  acc  add bab  bbc  bcd  bda cac  cbd  cca  cdb dad  dba  dcb  ddc II.    baa  bbb  bcc  bdd cab  cbc  ccd  cda dac  dbd  dca  ddb aad  aba  acb  adc
```

As will be appreciated one of skill in the art, the present application also encompasses concatenated sequence tokens having three or more unique sequence tokens, four or more unique sequence tokens and the like.

In addition, the sequence tokens can also be separated by a linker sequence. A suitable linker sequence will generally be a nucleic acid sequence that is not contained in the sequence tokens. For example, the sequence tokens of Groups I and II above both do not contain a GC nucleotide sequence. Therefore, a suitable linker to use with Group I and II sequence tokens is the Aci I restriction enzyme recognition site (CCGC). The advantage of this sequential ligation of tokens is to allow successive combination of pools of genomes in the labeling process described below, this is not stated explicitly and may be helpful to note.

For example, the ditokens can be synthesized of two adaptors: a left hand adaptor and a right hand adaptor, wherein each adaptor includes restriction enzyme recognition sites that can be used to liberate the sequence token. Examples of sequence tokens and the left hand and right hand adaptors are provided below:

Left Adaptor Sequence:

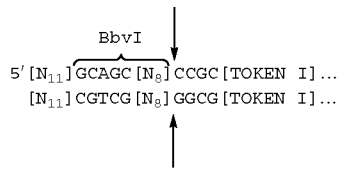

Right Adaptor Sequence:

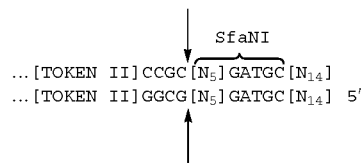

The oligonucleotides can be synthesized and then cloned into plasmids for validation by sequencing and then liberated using the corresponding restriction enzymes and ligated together and added to nucleic acid fragments.

Detection of Rare Alleles

As noted above, the sequence tokens of the present invention can be used to detect the presence or absence of rare alleles in a population. By "rare alleles" or "rare polymorphisms" is meant a mutation, including an insertion, deletion or substitution, as well as a single nucleotide polymorphism occurring at a low frequency in a population, such as at about 0.1% to about 5%, including about 0.2% to about 4.5%, about 0.3% to about 4%, about 0.4% to about 3.5%, about 0.5% to about 3%, and the like. Due to the low frequency of occurrence, rare alleles or rare single nucleotide polymorphisms have traditionally been difficult to identify. Unfortunately, conventional sequencing approaches do not have sufficient sensitivity to detect reliably rare alleles or mutant sequences in a pool of sequences when their abundances are less than a few percent. In order to have 95% confidence of identifying an allele with a 2% frequency, 75 individuals would need to be sequenced. In addition, detection of these alleles assumes the ability to detect heterozygote peaks in a sequencing trace with good accuracy. In contrast, the sequence tokens of the present invention permit the identification of rare alleles and/or mutations in pools, or mixed populations, of nucleic acid sequences, such as a pool of genomic sequences, which is advantageous in several fields, including genetics research, medical genetics, and oncology.

Prior to screening and detection of the presence or absence of a rare allele, the genomic DNA of population of individuals are each tagged with a unique concatenation of sequence tokens to enable subsequent identification and sorting of the population of DNA. However, based on the guidance provided herein, one of skill in the art will appreciate that a variety of unique tags can be constructed from the described sequence tokens. A schematic of an exemplary tagged genomic DNA fragment is provided in FIG. 2, panel A, and an exemplary concatenation process of sequence unique tokens is provided in FIG. 2, panel B.

As shown in FIG. 2A, the exemplary tagged genomic DNA fragment of approximately 1 kb includes a tag having a concatenation of four unique sequence tokens separated by a first functional sequence (A) with the tag and genomic DNA fragment being flanked by second (B) and third (C) functional sequences. In general, while the tags will be variable, e.g., unique, between the genomic DNA fragments of each individual, the functional sequences will be constant for all the genomic DNA fragments of all the individuals in the population. As used herein the "functional sequences" can include a variety of sequences that facilitate subsequent analysis and sorting, such as primer sequences, T7 RNA polymerase promoter sequence, and restriction enzyme recognition sites. For example, in some embodiments, the second (B) and third (C) functional sequences will include sequences complementary to forward and reverse primers to facilitate amplification of the entire tagged genomic DNA fragment or to make single stranded copies of the entire tagged genomic DNA fragment for analysis. In addition, in some embodiments, the first functional sequence (A) may also include a sequence complementary to a primer that is different than the primer of the second (B) or third (C) functional sequences. As a result, this additional primer sequence will allow amplification of only the genomic DNA fragment flanked by the first (A) and third (C) functional sequences without amplification of the sequence token tag. In addition, the first (A) functional sequence can also include a restriction enzyme recognition site that can facilitate liberation of the sequence token tag from the genomic DNA fragment.

The exemplary tagging system shown in FIG. 2B is based on a 4× concatenation dimensionality with an 8 sequence token base at each level to facilitate tagging of 4,096 (8×8×8×8=4096) individual genomes. In this system, a first set of 8 unique sequence tokens are used in the first position "P", a second set of 8 unique sequence tokens are used in the second position "Q", a third set of 8 unique sequence tokens are used in the third position "R", and a third set of 8 unique sequence tokens are used in the third position "S". Therefore, this exemplary system requires a total of 32 individual sequence tokens (8+8+8+8=32).

In order to achieve the tagging of the genomic DNA, first the 4,096 genomic DNA molecules are tagged in the first "P" position with the first set of 8 sequence tokens numbered 25 through 32 in repeating sequential order from 25 to 32. For example, the genomic DNA fragments from individual number 1 would be tagged in the "P" position with sequence token number 25 and would be classified as $P_{25}$, the genomic DNA fragments from individual number 2 would be tagged in the "P" position with sequence token number 26 and would be classified as $P_{26}$, the genomic DNA fragments from individual number 3 would be tagged in the "P" position with sequence token number 27 and would be classified as $P_{27}$, and so on though sequence token number 32 after which the tagging would be repeated (e.g., the genomic DNA fragments from individual number 9 would be tagged in the "P" position with sequence token number 25 and would be classified as $P_{25}$) until all the genomic DNA fragments from the 4,096 individuals or samples are tagged. Each set of $P_{25}$ through $P_{32}$ tagged samples are then pooled into a single $P_{25-32}$ group to provide 512 $P_{25-32}$ groups. For example, as shown in FIG. 2B, sample numbers 1 though 8 are pooled into a first 512 $P_{25-32}$ group, sample numbers 9 though 16 are pooled into a second 512 $P_{25-32}$ group, and etc.

The 512 $P_{25-32}$ groups are then tagged in the second "Q" position with the second set of 8 sequence tokens numbered 17 through 24 in repeating sequential order from 17 to 24. For example, the genomic DNA fragments from the first $P_{25-32}$ group would be tagged in the "Q" position with sequence token number 17 and would be classified as $Q_{17}P_{25-32}$, the genomic DNA fragments from the second $P_{25-32}$ group would be tagged in the "Q" position with sequence token number 18 and would be classified as $Q_{18}P_{25-32}$, the genomic DNA fragments from the third $P_{25-32}$ group would be tagged in the "Q" position with sequence token number 19 and would be classified as $Q_{19}P_{25-32}$, and so on though sequence token number 24 after which the tagging would be repeated (e.g., the genomic DNA fragments from the ninth $P_{25-32}$ group would be tagged in the "Q" position with sequence token number 17 and would be classified as $Q_{17}P_{25-32}$) until all the genomic DNA fragments from the 512 $P_{25-32}$ groups are tagged. Each set of $Q_{17}$ through $Q_{24}$ tagged samples are then pooled into a single $Q_{17-24}P_{25-32}$ group to provide 64 $Q_{17-24}P_{25-32}$ groups. For example, as shown in FIG. 2B, sample groups 1 though 8 are pooled into a first 64 $Q_{17-24}P_{25-32}$ group, groups 9 though 16 are pooled into a second 64 $Q_{17-24}P_{25-32}$ group, and etc.

The 64 $Q_{17-24}P_{25-32}$ groups are then tagged in the third "R" position with the third set of 8 sequence tokens numbered 9 through 16 in repeating sequential order from 9 to 16. For example, the genomic DNA fragments from the first $Q_{17-24}P_{25-32}$ group would be tagged in the "R" position with sequence token number 9 and would be classified as $R_9 Q_{17-24}P_{25-32}$, the genomic DNA fragments from the second $Q_{17-24}P_{25-32}$ group would be tagged in the "R" position with sequence token number 10 and would be classified as $R_{10} Q_{17-24}Q_{18}P_{25-32}$, the genomic DNA fragments from the third $Q_{17-24}P_{25-32}$ group would be tagged in the "R" position with sequence token number 11 and would be classified as $R_{11} Q_{17-24}P_{25-32}$, and so on though sequence token number 16 after which the tagging would be repeated (e.g., the genomic DNA fragments from the ninth $Q_{17-24}P_{25-32}$ group would be tagged in the "R" position with sequence token number 9 and would be classified as $R_9 Q_{17-24}P_{25-32}$) until all the genomic DNA fragments from the 64 $Q_{17-24}P_{25-32}$ groups are tagged. Each set of $R_9$ through $R_{16}$ tagged samples are then pooled into a single $R_{9-16}Q_{17-24}P_{25-32}$ group to provide 8 $R_{9-16}Q_{17-24}P_{25-32}$ groups. For example, as shown in FIG. 2B, sample groups 1 though 8 are pooled into a first $R_{9-16}Q_{17-24}P_{25-32}$ group, groups 9 though 16 are pooled into a second $R_{9-16}Q_{17-24}P_{25-32}$ group, and etc.

The 8 $R_{9-16}Q_{17-24}P_{25-32}$ groups are then tagged in the fourth "S" position with the fourth set of 8 sequence tokens numbered 1 through 8 in repeating sequential order from 1 to 8. For example, the genomic DNA fragments from the first $R_{9-16}Q_{17-24}P_{25-32}$ group would be tagged in the "S" position with sequence token number 1 and would be classified as $S_1 R_{9-16}Q_{17-24}P_{25-32}$, the genomic DNA fragments from the second $R_{9-16}Q_{17-24}P_{25-32}$ group would be tagged in the "S" position with sequence token number 2 and would be classified as $S_2 R_{9-16}Q_{17-24}Q_{18}P_{25-32}$, the genomic DNA fragments from the third $R_{9-16}Q_{17-24}P_{25-32}$ group would be tagged in the "S" position with sequence token number 3 and would be classified as $S_3 R_{9-16}Q_{17-24}P_{25-32}$, and so on though sequence token number 8 until all the genomic DNA fragments from the 8 $R_{9-16}Q_{17-24}P_{25-32}$ groups are tagged. The tagged samples are then pooled into a single $S_{1-8}R_{9-16}Q_{17-24}P_{25-32}$ pooled population of uniquely tagged genomic DNA fragments from 4,096 different samples.

As a result of the unique sequence token tagging system the correct sample identification of any tagged genomic DNA fragment removed from the pooled population can be readily determined based on the sequence tokens at each of the S, R, Q, and P positions. For example, a genomic fragment tagged with sequence tokens $S_1 R_9 Q_{17} P_{29}$ is identified as being from original sample number 5 (FIG. 2B).

Figure 2:
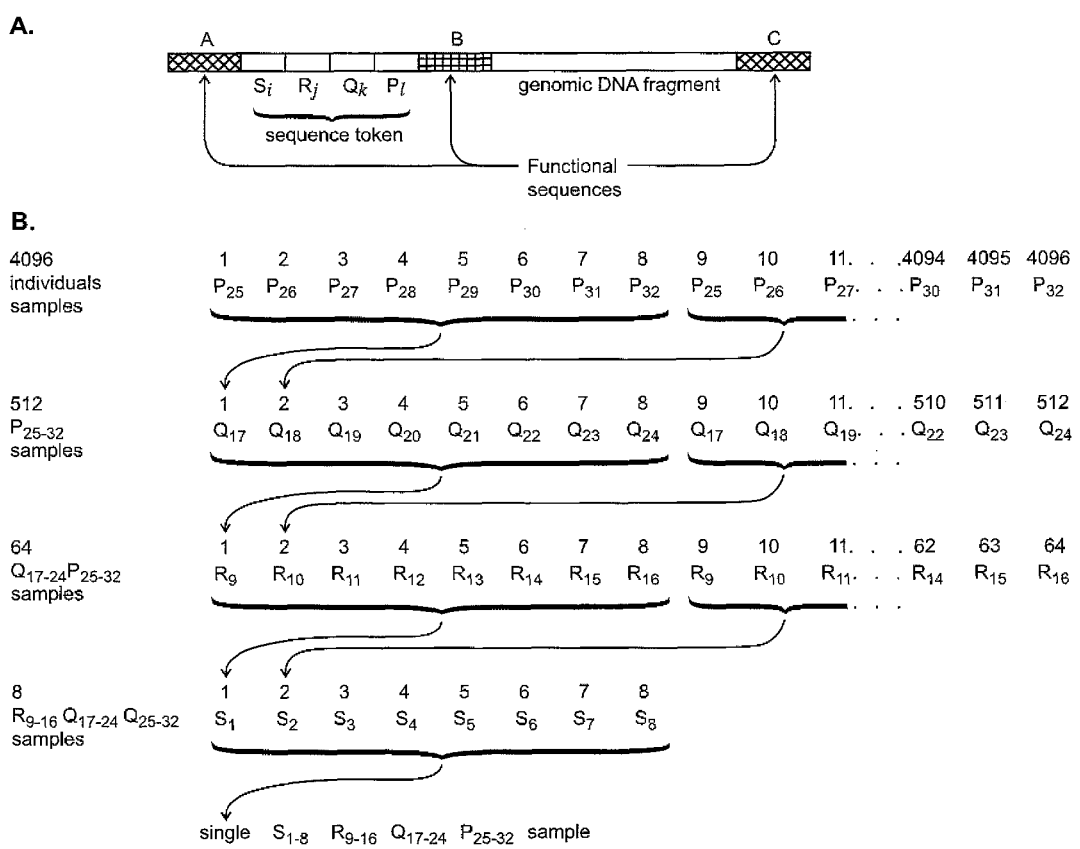
FIG. 2 shows a schematic of an exemplary tagged genomic DNA fragment panel A and an exemplary concatenation process of sequence unique tokens in panel B.
Figure 3:
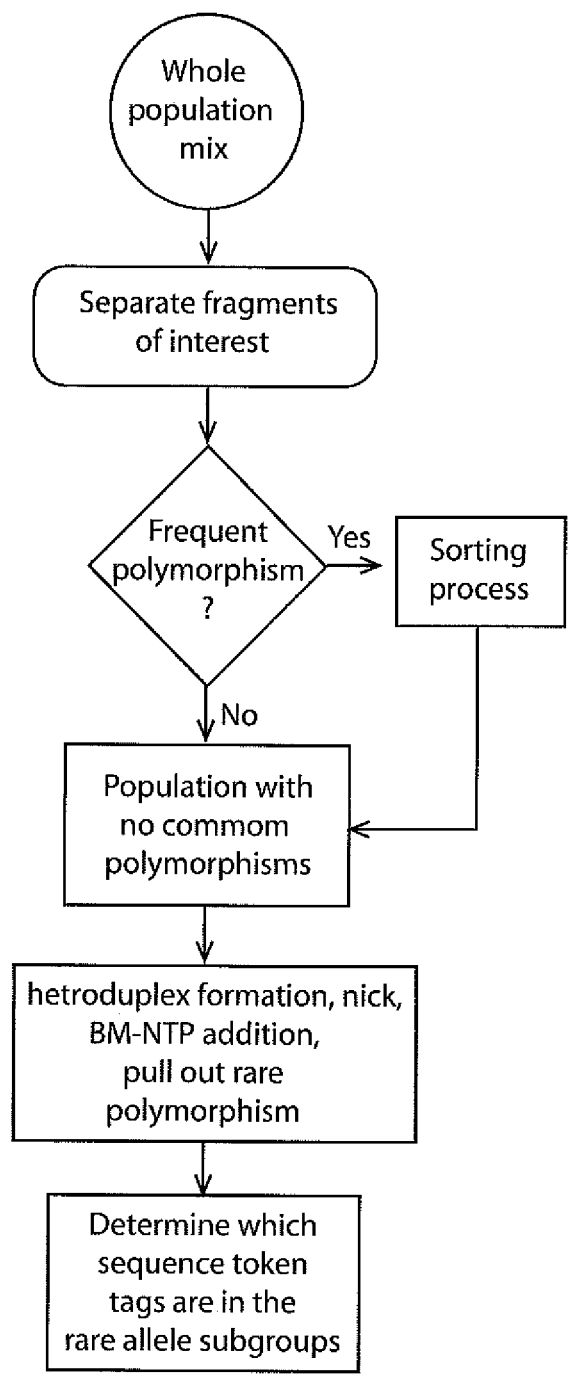
FIG. 3 provides a schematic diagram of a method for identifying individuals or samples carrying a rare allele by using the sequence token tagging system.

FIG. 3 provides a schematic diagram of a method for identifying individuals or samples carrying a rare allele by using the sequence token tagging system. Prior to analysis of the tagged nucleic acid population, a single stranded copy of all the tagged nucleic acids is produced. The single strand copies of the tagged nucleic acid population be produced by, for example, using a priming sequence provided in the third functional sequence (C) (FIG. 2A).

In certain embodiments in which the number of samples in a given population of tagged nucleic acids is high and/or the particular rare allele occurs at a low frequency, then it may be desirable to enrich the sample of tagged nucleic acids for only the tagged nucleic acid fragments that include the sequence of interest that carries the rare allele. This enrichment can be done by, for example, using a probe that is complementary to a sequence of interest. For example, if the rare allele of interest is known to be present in a particular gene, such as the p53 gene, an oligonucleotide probe can be used that is complementary to a sequence found in the gene of interest to facilitate separation of the sequence token tagged fragments carrying the gene of interest by hybridization. As a result, the separation provides an enriched population of tagged nucleic acid fragments encoding the gene of interest in order to remove other sequence token tagged nucleic acids that may interfere in the subsequent analysis.

For example, in some embodiments, an oligonucleotide probe that is complementary to a fragment of interest can be constructed to include a first member of a binding pair to facilitate separation of the tagged nucleic acid fragments of interest. Exemplary binding pairs include, but are not limited to, biotin and avidin, biotin and streptavidin, and the like. Other binding elements that can also be used to separate fragments of interest include magnetic beads, such as DYNA-BEADS™. In such embodiments, the oligonucleotide probes are immobilized to the first binding member of the binding pair, such as biotin, avidin, streptavidin, or a magnetic bead, and the probes are then incubated with the sample of tagged nucleic acid population under condition that allow hybridization between the oligonucleotide probes and the fragments if interest. Following an adequate amount of time, the hybridized probes as well as the tagged fragments of interest can be separated from the remaining population of tagged nucleic acids using the second member of the binding pair, such as avidin or streptavidin if biotin is used, or a magnet if a magnetic bead is used.

In some embodiments, it may be desirable to perform further enrichment selections to ensure only tagged nucleic acid encoding the fragment of interest are present in the enriched sample for the analysis. In such embodiments, a second oligonucleotide probe can be used that is complementary to a second sequence on the fragment of interest that is different than the sequence complementary to the first oligonucleotide probe. The addition enrichment steps can be repeated as necessary to provide the desired enrichment level to avoid contamination with tagged nucleic acids that do not contain the fragment of interest. In yet another embodiment, such fragments of interest could be rescued from the mixture of all fragments by using two PCR primers (one of which is labeled with a specific ligand such as, but not restricted to, biotin) which amplify only the fragment of interest. The amplicon resulting could then be isolated by binding of the ligand-bearing PCR fragment to a solid phase coated with its binding pair complement (which is streptavidin in the case of biotin).

As shown in FIG. 3, a second type of enrichment step can also be carried out in addition to the above-described separation step that provides for separation the sample population based on highly frequent alleles that may also be present in close proximity to a rare allele that may interfere with identification of samples that contain the rare allele. Such "frequent alleles" or "frequent polymorphisms" include a mutation, such as an insertion, deletion, or substitution, as well as a single nucleotide polymorphism occurring at a high frequency in a population, such as at about 5% or more, usually about 10% or more.

Figure 4:
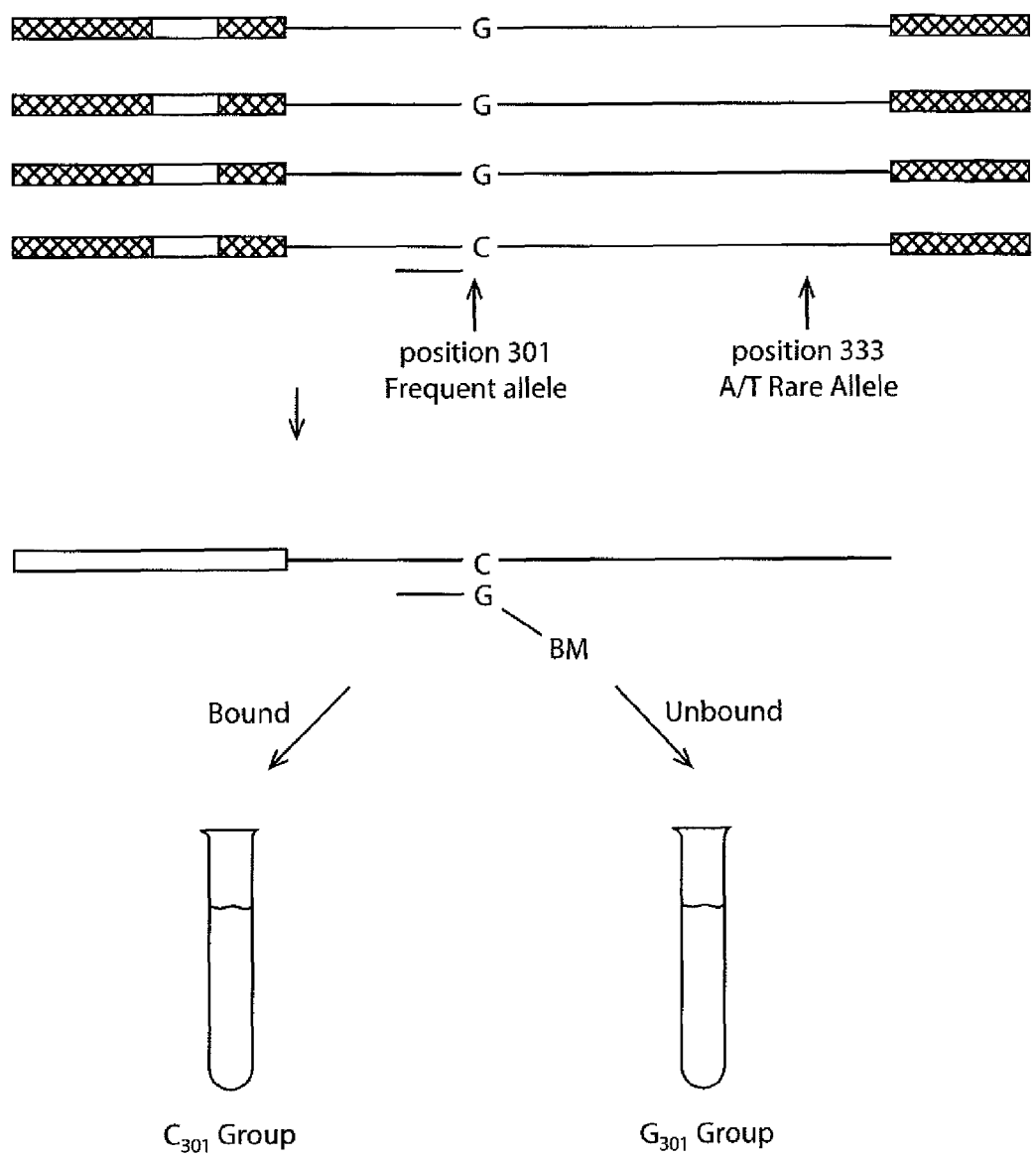
FIG. 4 provides a schematic depiction of how the tagged nucleic acid population can first be separated into frequent allele groups prior to analysis of the presence or absence of a rare allele.

FIG. 4 provides a schematic depiction of how the tagged nucleic acid population can first be separated into frequent allele groups prior to analysis of the presence or absence of a rare allele. In the depicted example, the rare allele of interest is known to exist at position 333; however, a frequent allele is also known to exist at position 301. The two variants of the single nucleotide polymorphism of the frequent allele are a C at position 301 or a G at position 301. In such an embodiment, it would be desirable to divide the population of tagged nucleic acids into two groups—the first group having a C at position 301 and the second group having a G at position 301. The two different groups can then be analyzed for the presence or absence of the rare allele.

In some embodiments, an oligonucleotide primer can be used that is complementary to a sequence at least one nucleotide upstream of the frequent polymorphism. The oligonucleotide primer and the tagged nucleic acids are incubated with a polymerase and necessary ddNTPs to provide extension of the oligonucleotide primer. In order to facilitate separation, the ddNTP corresponding to one form of the frequent SNP can be conjugated to a binding member (BM) and upon extension the particular ddNTP-BM is incorporated into the oligonucleotide primer. The BM can then be used to separate the two groups of the SNPs. The binding members, as described above can be, for example, biotin, avidin, streptavidin, magnetic beads, and the like.

As shown in the example in FIG. 4, to separate the tagged nucleic acids based on the SNP occurring at position 301, an oligonucleotide primer is used that is complementary to a sequence terminating at position 300. The tagged nucleic acids and oligonucleotide, ddCTP and ddGTP-BM are incubated with a polymerase under conditions to allow incorporation of the nucleotides in to oligonucleotide primer. Based on either the presence of G or C at position 301, either C or G-BM will be incorporated into the oligonucleotide primer. Following an adequate amount of time to allow extension, the population of heteroduplexed tagged nucleic acids and extended oligonucleotide probes are separated based on the binding moiety incorporated in the oligonucleotide probes. As a result, the tagged population will be divided into two groups—the $C_{301}$ group and the $G_{301}$ group. The two groups can then be separately analyzed for the presence or absence of the rare allele.

Separation of the tagged nucleic acids containing the rare the allele can be carried out in a similar manner to separation of the initial pool of tagged nucleic acids based on frequent alleles as described above. In the depicted example of FIG. 4, the rare allele of interest is known to exist at position 333. The two variants are either an A at position 333 or a T at position 333 with the rare variant being the A at position 333. In such an embodiment, the population of tagged nucleic acids would be sorted to remove the tagged nucleic acids having the A at position 333 and then identifying which samples the particular tagged nucleic acids originated from using the unique sequence token tags.

In some embodiments, an oligonucleotide primer can be used that is complementary to a sequence at least one nucleotide upstream of the rare polymorphism present at a known position in the fragment. The oligonucleotide primer and the tagged nucleic acids are incubated with a polymerase and necessary ddNTPs to provide extension of the oligonucleotide primer. In order to facilitate separation, the ddNTP corresponding to the rare variant of the SNP is conjugated to a binding member (BM) and upon extension the particular dNTP-BM is incorporated into the oligonucleotide primer. The BM can then be used to separate tagged nucleic acids having the rare variant of the SNP from the tagged nucleic acids that do not. The binding members, as described above can be, for example, biotin, avidin, streptavidin, magnetic beads, and the like. To separate the tagged nucleic acids based on the SNP occurring at position 333, an oligonucleotide primer is used that is complementary to a sequence up position 332. The tagged nucleic acids and oligonucleotide, ddATP and ddTTP-BM are incubated with a polymerase under conditions to allow incorporation of the nucleotides in to oligonucleotide primer. Based on either the presence of T or the rare A at position 333, either A or T-BM will be incorporated into the oligonucleotide primer. Following an adequate amount of time to allow extension, the population of heteroduplexed tagged nucleic acids and extended oligonucleotide probes are separated based on the binding moiety incorporated in the oligonucleotide probes. As a result, the tagged nucleic acids having the rare A polymorphism at position 333 can be separated from the remaining tagged nucleic acids based on the binding moiety and analyzed to determine which from original samples the tagged nucleic acids originate.

Figure 5:
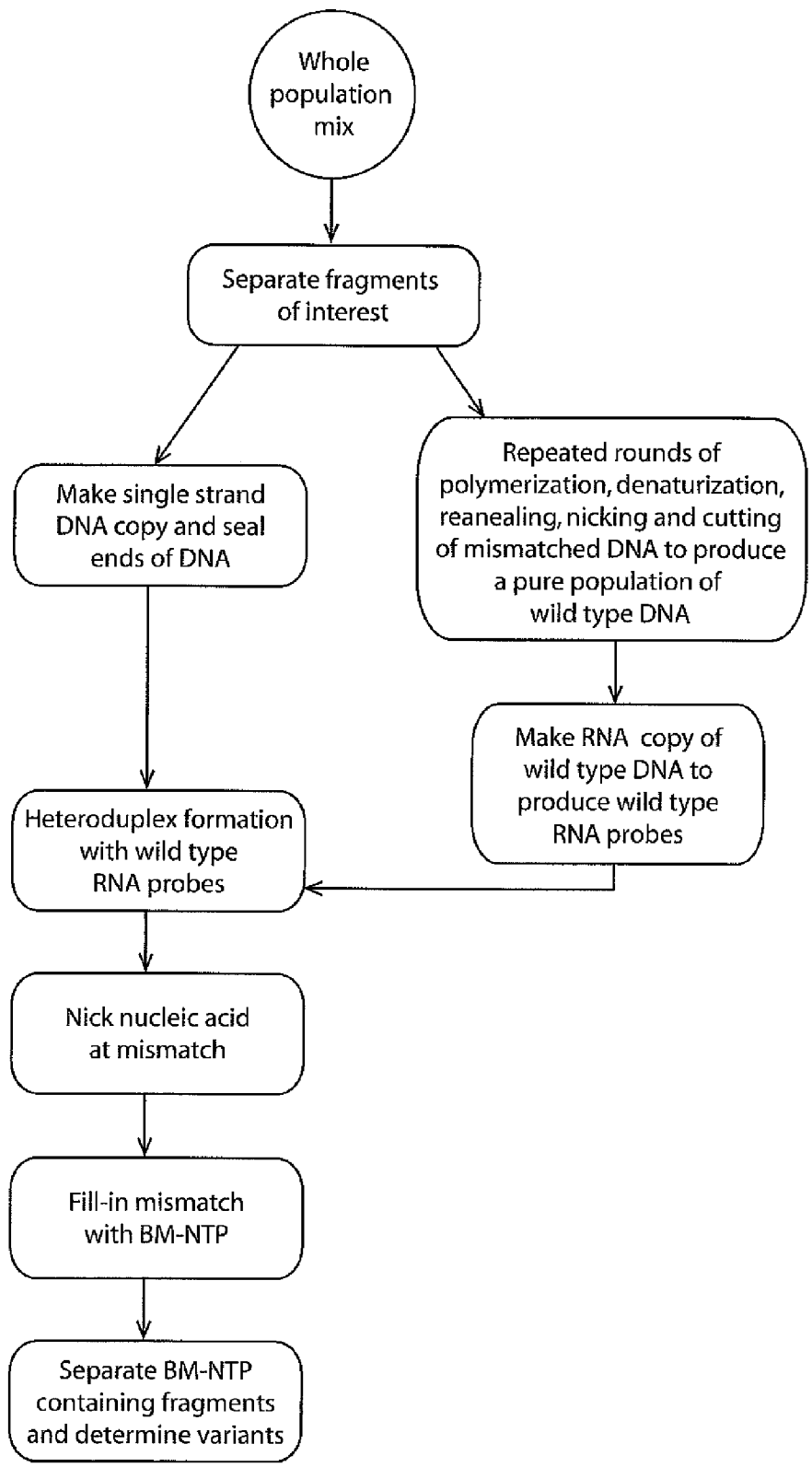
FIG. 5 provides a schematic diagram of a method for identifying individuals or samples carrying a rare allele by using the sequence token tagging system and wild type RNA probes.

An alternative method of detecting a rare polymorphism is to form heteroduplex molecules using wild type RNA probes. A schematic diagram of the exemplary method is provided in FIG. 5. As in the example above, the whole population of sequence token tagged nucleic acids may optionally be enriched to provide the sequence token tagged nucleic acid fragments that include the sequence of interest that carries the rare allele. As described above, the enrichment step can be performed by, for example, using labeled oligonucleotide probes complementary to a nucleic acid sequence known to exist in the nucleic acid fragment of interest. As a result, the separation provides an enriched population of tagged nucleic acid fragments encoding the gene of interest in order to remove other sequence token tagged nucleic acids that may interfere in the subsequent analysis. Following the optional enrichment step, single stranded DNA copies of the sequence token tagged fragments of interest are made. In general, the single stranded DNA copies will include the nucleic acids fragments as well as the sequence token tags.

The enriched population of wild type RNA probes can be generated by, for example, denaturization of the DNA, reannealing, nicking and digestion of mismatched DNA to remove all nucleic acid fragments having the rare polymorphism and to provide a population of nucleic acids substantially lacking the rare polymorphism. For example, the sequence token tagged nucleic acids fragments of interest are treated with one or more restriction enzymes to liberate the nucleic acid fragments from the sequence tokens and the functional sequences (e.g., functional sequences A, B, and C (FIG. 2, panel A)). As noted above functional sequences B and C can be designed to incorporate restriction enzyme recognition sites that Alternatively, liberation of the nucleic acid fragments from the sequence tokens and the functional sequences can also be carried out by repeated rounds of DNA amplification using primer sequences complementary to nucleic acid sequences in the functional sequences B and C (FIG. 2, panel A). Following amplification, the single stranded material can be digested by treating the sample with a nuclease, such as SI nuclease.

After liberation of the nucleic acid fragments from the sequence token tags, the nucleic acid fragments are subjected to denaturization of the DNA, reannealing, nicking and digestion of mismatched DNA to remove all nucleic acid fragments having the rare polymorphism. For example, the nucleic acids are denatured and reannealed to allow the nucleic acid fragments having the rare polymorphism to hybridize to nucleic acid fragments lacking the rare polymorphism. In general, the method is based on the principle that since the nucleic acid fragments having the rare polymorphism will be in a low concentration in the sample, such as on the order of 0.1% to about 5%, the nucleic acid fragments not carrying the rare polymorphism will be in excess and will drive the reaction towards dilution of the rare polymorphism encoding nucleic acid fragments. Once the nucleic acid fragments have been allowed to reanneal, the mixture is treated with a nuclease, such as SI nuclease, that will digest any single stranded nucleic acids as well as nick and hydrolyze any mismatched double stranded nucleic acids. Any double stranded nucleic acids having a first strand that includes the rare polymorphism and a second strand that lacks the rare polymorphisms will result in a mismatch at the rare polymorphism. As a result, these hybrid double stranded nucleic acids will be nicked at the rare polymorphism mismatch and the both strands of the hybrid molecule will be hydrolyzed. Therefore, due to the denaturization, reannealing, nicking and digestion of mismatched DNA, the rare polymorphism containing nucleic acids (hybrid molecules) will be diluted out to provide a substantially pure composition of nucleic acid fragments lacking the rare polymorphism. The denaturization, reannealing, and digestion of mismatched DNA can also be optionally repeated to further dilute the rare polymorphism containing nucleic acids. Once a substantially pure population of nucleic acid fragments lacking the rare polymorphism is produced, the nucleic acid fragments are treated with a RNA polymerase to produce single stranded RNA probes of the nucleic acids lacking the rare polymorphism.

The single stranded RNA probes of the nucleic acids lacking the rare polymorphism are then combined with the DNA copy of the enriched nucleic acid fragments, the mixture allowed to denature and anneal to form heteroduplexes of RNA and DNA (FIG. 4). Any double stranded heteroduplex molecules in the composition having a DNA strand that includes the rare polymorphism and a RNA strand lacking the rare polymorphisms will result in a mismatch at the rare polymorphism. The heteroduplex molecules are then treated with RNAse I to nick the RNA molecules at the mismatch, remove the mismatch nucleotide, and produce a 3' phosphate on the nicked RNA strand. The 3' phosphate can then be removed using alkaline phosphatase and using a polymerase, such as T7 sequence, BM-NTP is incorporated at the site of the nick. The BM can then be used to separate tagged nucleic acids having the rare variant of the SNP from the tagged nucleic acids that do not. The binding members (BM), as described above can be, for example, biotin, avidin, streptavidin, magnetic beads, and the like.

The identify of the tagged nucleic acids can be determined by sequentially sequencing the sequence tokens at each position beginning with the S group, then the R, Q, and P groups. For example, a first sequencing primer will be used that is complementary to the first functional sequence (A, FIG. 2A) to determine the S position sequence tokens. Once the S position sequence tokens are determined, the remaining sequence tokens are also sequenced using sequencing primers that are complementary to the upstream sequence token. For example, if the sequencing reveals that two types of S position sequence token are found, e.g., $S_1$ and $S_5$, in the sorted population, then the second step sequencing will utilize sequencing primers that are complementary to the sequences of the $S_1$ and $S_5$ sequence tokens. Once all the samples are sorted out, the positioning of the specific sequence tokens at each position $S_{1-8}R_{9-16}Q_{17-24}P_{25-32}$ are decoded to determine the identify of the samples encoding the rare alleles. For example, if the analysis reveal that the only sequence token present is $S_1R_9Q_{17}P_{29}$ then it can be determined that only sample number 5 contains the rare allele.

Sieving Devices

In one aspect, sorting of the sequence tokens tagged nucleic acid fragments can be carried out by using a series of gates represented by the complements of the sequence tokens. Tags containing a particular sequence token would be stopped (e.g. by hybridization) at the gate corresponding to its complement, all others would be let through. Since this would rely on 100% yield at each gate, this would not be an efficient use of sequence tokens. Instead, a sorting technique is used wherein a collection of tagged DNAs would be divided into two groups, one group containing a particular sequence token, the other group lacking the specific such token. An exemplary sorting technique suitable for use with the present invention is the sorting technique described in Brenner, PCT publication number WO 2005/080604, which is incorporated herein by reference. In the described sorting technique, populations can be sorted independent of yield. Since oligonucleotide tags of the invention do not include repeats of sequence tokens, they can be sorted in a binary sorting process as described below, which will be referred to herein as a "sieve." As such, sequence tokens of a subset can be identified by a sieving process, where a series of steps are carried out in which a subset (which may be in the form of a concatenation of sequence tokens) is sorted at each step into those subsets that have a particular sequence token and those that do not.

In particular, the device includes a reusable solid phase support such as linear element, e.g., a pin, that carries a chemically stable anti-sequence token that is complementary to a specific sequence token, or a portion thereof in instances of concatenated sequence tokens, present in the population mixture. The chemically stable anti-sequence token can be a nucleic acid analogue sequence, such as a peptide nucleic acid, a nucleic acid with a non-charged backbone or a locked nucleic acid (LNA). This allows for an improved rate and specificity of the hybridization event with the sequence token. The linear element, such as the pin, can be fabricated out of any suitable material, such as plastic, that will provide for desirable results and will not interferes with the hybridization event. The linear element can be fabricated to either indirectly or directly carry the anti-sequence token. For example, the sequence token may be immobilized directly to the surface or the linear element. Alternatively, the sequence token may be immobilized to the surface of a secondary element, such as a glass or plastic beads that then attached to the linear element. In some embodiments, the linear elements may be constructed of fiber optic fragments that are attached directly or indirectly to a detection means. Anti-token sequences can be synthesized individually and then immobilized to either the linear element or the secondary element that is then attached to the linear element.

In certain embodiments, the linear elements are arranged in a comb-like manner, wherein each linear element has immobilized thereon an anti-token oligonucleotide that is complementary to a specific sequence token. The combs of linear elements may be further arranged and immobilized in a block to provide an addressable array of linear elements, such as pins, wherein each linear element extending away from the block has immobilized thereon, either directly or indirectly as described above, an anti-token oligonucleotide that is complementary to a specific sequence token. The block of addressable linear elements may further be connected to solution pumping and delivery means, wherein each linear element and the respective immobilized anti-sequence token is brought into fluid communication with a solution containing the sequence token tagged nucleic acid fragments.

In further embodiments, the addressable block of linear elements may be positioned in a robotic arm that is controlled by a programmable means that provides for movement of the addressable block from a first position to a second position, such as a first plate having channels or a plurality of wells, such as a first microliter plate, to a second plate having channels or a plurality of wells, such as a second microliter plate. In other embodiments, the addressable block remains stationary while the plates are positioned in a robotic arm that provides for movement of the plates from a first position to a second position.

As noted above, the sieving device can be used to sort out at individual steps a population of sequence token tagged genomes into those subsets that have a particular sequence token and those that do not. To carry out the methods using the sieving device, the individual genomes must first be tagged with sequence tokens. For example, 16 individual sequence tokens in a 3× concatenation system can be used to tag 4,096 (16×16×16=4096) individual genomes. In this system, a first set of 16 unique sequence tokens are used in the first position "P", a second set of 16 unique sequence tokens are used in the second position "Q", and a third set of 16 unique sequence tokens are used in the third position "R". Therefore, this exemplary system requires a total of 48 individual sequence tokens (16+16+16=48). Alternatively, 8 individual sequence tokens in a 4× concatenation system can also be used to tag 4,096 (8×8×8×8=4096) individual genomes. This alternative exemplary system requires a total of 32 individual sequence tokens (8+8+8+8=32).

In order to achieve the tagging of the genomic DNA, first the 4,096 genomic DNA molecules are sorted into 16 "P" groups, i.e., groups $P_1$, $P_2$, $P_3$, etc. The nucleic acids in each "P" group are tagged with the first set of 16 sequence tokens numbered 33 through 48. As such, the nucleic acids of group $P_1$ are all tagged with sequence token number 33, the nucleic acids of group $P_2$ are all tagged with sequence token number 34, the nucleic acids of group $P_3$ are all tagged with sequence token number 35, the nucleic acids of group $P_4$ are all tagged with sequence token number 36, etc. The "P" groups are then recombined and sorted again into 16 "Q" groups, i.e., groups $Q_1$, $Q_2$, $Q_3$, etc. The nucleic acids in each "Q" group are tagged with the second set of 16 sequence tokens numbered 17 through 32. As such, the nucleic acids of group $Q_1$ are all tagged with sequence token number 17, the nucleic acids of group $Q_2$ are all tagged with sequence token number 18, the nucleic acids of group $P_3$ are all tagged with sequence token number 19, the nucleic acids of group $Q_4$ are all tagged with sequence token number 20, etc. The "Q" groups are then recombined and sorted again into 16 "R" groups, i.e., groups $R_1$, $R_2$, $R_3$, etc. The nucleic acids in each "R" group are then tagged with the third set of 16 sequence tokens numbered 1 through 16. As such, the nucleic acids of group $R_1$ are all tagged with sequence token number 1, the nucleic acids of group $R_2$ are all tagged with sequence token number 2, the nucleic acids of group $R_3$ are all tagged with sequence token number 3, the nucleic acids of group $R_4$ are all tagged with sequence token number 4, etc. A similar tagging system can also be achieved by directly tagging all 4,096 genomes with 4,096 different sequence tokens. As will be appreciated by one of skill in the art, the order of the sequence tokens is not significant. For example, sequence tokens 1 though 16 can be used for the P groups, sequence tokens 17 though 32 can be used for the Q groups, and the sequence tokens 33 though 48 can be used for the R groups.

In such an exemplary method, the sieving device would be fabricated to be capable of separating the tagged nucleic acids into the 4,096 individual genomes. The sieving device is particularly useful for allowing subgrouping and subsequent detection and identification of individuals carrying a genetic variation, such as a rare allele and/or single nucleotide polymorphism, against a large background of other polymorphisms. In carrying out the exemplary methods, a population of tagged nucleic acids is first sorted based on the sequence of the genomic DNA to provider an enriched population of tagged genomic DNA. For example, a probe complementary to a nucleic acid sequence interest, such as a gene, can be used to select all tagged nucleic acids in a population that encode the nucleic acid sequence of interest. As a result, the tagged genomic fragment from all individuals in the population encoding the nucleic acid sequence of interest would be sorted into an enriched population for further analysis as described in greater detail above. Once the nucleic acids have been analyzed, the sieving device can be used to determine the identity of the individuals in a subgroup of tagged nucleic acids.

In general, the size of the final linear elements and the number of molecules that immobilized on each linear element will vary depending on the sensitivity of the detection system. In general, the number of molecules immobilized to each linear element will be from about $10^4$ molecules to about $10^{15}$ molecules or more, including about $10^5$ molecules to about $10^{12}$ molecules, such as about $10^8$ molecules. In certain embodiments, for example, the number of molecules capable of binding to each linear element will be approximately $10^8$ molecules, which can be immobilized to an area of between 2,500 µm² and about 10,000 µm² (an area of approximately 50-100 µm by 50-100 µm) at a density of approximately one molecule per 50 to 100 Å². As such, the molecules may be immobilized to beads or pins of approximately 10 to 100 µm in diameter. The linear elements, such as pins will generally have a diameter of approximately 0.25 mm (250 µm) spaced apart by a similar distance, such as 0.25 mm (250 µm).

Prior to use of the sieving device to determine the identity of the individuals in a subgroup of tagged genomic DNA, the genomic DNA portion may optionally be removed to avoid interference of sequences in the genomic DNA with hybridization events between the sequence tokens and complementary anti-sequence tokens immobilized on the linear elements of the sieving device.

Figure 6:
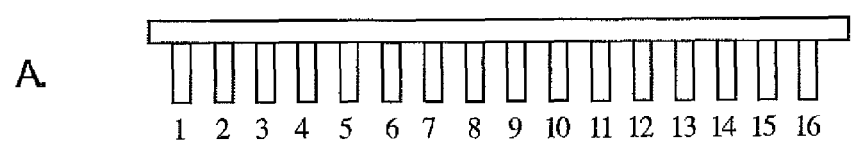
FIG. 6 shows schematic diagrams of an exemplary sieving device. Panel A shows arrangement of the linear elements, or pins, each having an anti-sequence token immobilized thereon and arranged in a comb-like manner. Panel B shows the bottom view a series of the combs arranges in a block. Panes C and D show cross-sections of a comb placed in a channel where the immobilized anti-sequence token can come into contact with the population of sequence tokens.
Figure 6:
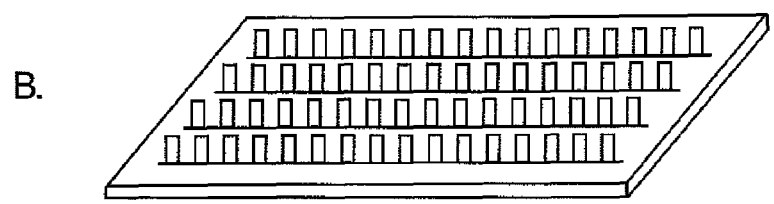
Figure 6:
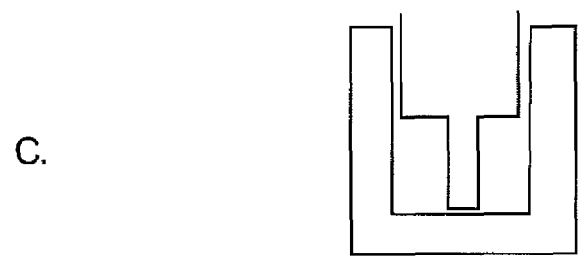
Figure 6:
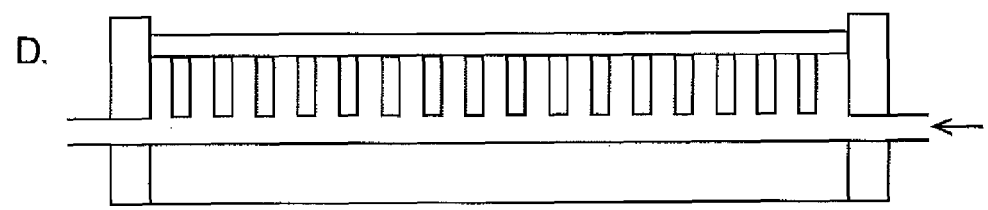

In order to effect the separation and sorting of the sequence tokens, the linear elements, or pins, can be arranges in a comb-like manner (FIG. 6, panel A) and arranged on a block in an addressable manner (FIG. 6, panel B). For example a first comb having 16 linear elements will have anti-sequence tokens complementary to sequence tokens 1 to 16 immobilized on the linear elements in an addressable manner. For example, a first comb will include anti-sequence tokens complementary to sequence tokens 1 to 16 of the 16 "R" groups, i.e., groups $R_1$, $R_2$, $R_3$, etc., a second comb will include anti-sequence tokens complementary to sequence tokens 17 to 32 of the 16 "Q" groups, i.e., groups $Q_1$, $Q_2$, $Q_3$, etc., and a third comb will include ant-sequence tokens complementary to sequence tokens 33 to 48 of the 16 "P" groups, i.e., groups $P_1$, $P_2$, $P_3$, etc. FIG. 6, panel 13, shows the bottom view of an exemplary structure of a block having addressable combs. As a result, the block will have anti-sequence tokens complementary to the 48 sequence tokens arranged in an addressable manner.

During use, each comb is positioned in a channel though which a solution containing the sequence token is pumped thereby allowing each of the linear elements of the comb to come into contact with the solution under conditions suitable for allowing hybridization to occur between the sequence tokens and the corresponding complementary anti-sequence tokens. Cross-sections of a comb placed in a channel are depicted in FIG. 6, panels C and D. As each pin comes into close contact with a sequence token complementary to the anti-sequence token immobilized thereon, hybridization occurs and the solution of sequence tokens is divided among the linear elements on the comb. The comb is then transferred to a series of wells containing a buffer solution, wherein each linear member is positioned in a different well. The temperatures of the wells are then increased to allow denaturization of the hybridized sequence tokens into the separate wells. As a result of the first sieving process, the solution of sequence tokens is separated into a plurality of groups based on the first sequence token position. For example, if using the system described above, the sample will be divided into the 16 "P" groups, i.e., groups $P_1$, $P_2$, $P_3$, etc., using the anti-sequence tokens immobilized on the linear elements that are complementary to sequence tokens 33 to 48. Each of the "P" group members are then subjected to a second round of sorting using a "Q" specific comb having the anti-sequence tokens immobilized on the linear elements that are complementary to sequence tokens 17 to 32. As a result, the initial population of sequence tokens will be sorted into 256 "Q-P" subpopulations (16×16). Each of the 256 "Q-P" group members are then subjected to a third round of sorting using a "R" specific comb having the anti-sequence tokens immobilized on the linear elements that are complementary to sequence tokens 1 to 16. As a result, the population of sequence tokens will be sorted into 4,096 "R-Q-P" subpopulations (256×16). In certain embodiments, the combs used for the third or final sorting step are fabricated of optic fibers that are capable of transmitting a detectable signal to a receiving unit. In such embodiments, the sequence tokens can be modified to carry a detectable moiety, such as a fluorescent protein. As a result, the presence or absence of the sequence token hybridized to the complementary anti-sequence token immobilized at each linear element can be readily assayed.

Kits and Systems

Also provided by the subject invention are kits for practicing the subject methods, as described above, such as combs having an array of immobilized anti-sequence tokens each specific for a unique sequence token of a nucleic acid tag. In some embodiments, the kits contain programming means to allow a robotic system to perform the subject methods, e.g., programming for instructing a robotic pipettor to add, mix and remove reagents, as described above. The various components of the kit may be present in separate containers or certain compatible components may be precombined into a single container, as desired.

The subject kits may also include one or more other reagents for preparing or processing an oligonucleotide tag of sequence tokens according to the subject methods. The reagents may include one or more matrices, solvents, sample preparation reagents, buffers, desalting reagents, enzymatic reagents, denaturing reagents, where calibration standards such as positive and negative controls may be provided as well. As such, the kits may include one or more containers such as vials or bottles, with each container containing a separate component for carrying out a sample processing or preparing step and/or for carrying out one or more steps of a combinatorial library synthesis protocol suing nucleic acid tags.

In addition to above-mentioned components, the subject kits typically further include instructions for using the components of the kit to practice the subject methods, e.g., to identify the presence or absence of a rare allele using the subject sieving device according to the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the subject database, programming and instructions, the kits may also include one or more control analyte mixtures, e.g., two or more control samples for use in testing the kit.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

That which is claimed is:

1. A composition comprising a mixture of polynucleotides, wherein the polynucleotides in the mixture are made by combining a plurality of different polynucleotide samples, wherein:
   each of the different samples comprises non-overlapping segments of a genome, wherein each of the non-overlapping segments is attached to a sequence tag that identifies the sample from which that segment is derived; and
   each of the sequence tags comprises two or more unique token sequences, wherein the token sequences are chosen from different sets of token sequences, and within each set, the token sequences are different from one another and are designed to not cross hybridize with one another or their complements.

2. The composition of claim 1, wherein said genome is a mammalian genome.

3. The composition of claim 1, wherein said genome is a human genome.

4. The composition of claim 1, wherein said genome is a viral genome.

5. The composition of claim 1, wherein said plurality of different polynucleotide samples is at least 10 different polynucleotide samples.

6. The composition of claim 1, wherein each of said sequence tags is at least 9 bases in length.

7. The composition of claim 1, wherein each token sequence within each set has the same number of s bases and w bases, wherein s is G or C and w is A or T.

8. The composition of claim 1, wherein each different token sequence has no adjacent GC pairs.

9. The composition of claim 1, wherein no token sequence is contained in two different sets of token sequences.

10. The composition of claim 1, wherein each of the different token sequences comprises a unique combination of triplet units selected from multiple different groups of triplet units, wherein each of said groups of triplet units has four members, and wherein each member of a group of triplet units is different from the other members of the same group by at least 2 out of 3 bases.

11. The composition of claim 10, wherein each of the different token sequences comprises a unique combination of at least three of the triplet units.

12. The composition of claim 10, wherein the multiple groups of triplet units are:

```
Group I   (sww): CAA, GAT, CTT, GTA;
Group II  (wsw): TGA, AGT, TCT, ACA;
Group III (wws): TAG, AAC, TTC, ATG;
Group IV  (www): TAA, AAT, TTT, ATA;
and
Group V   (sws): CAG, GAC, CTC, GTG.
```

13. The composition of claim 11, wherein the polynucleotides from each of the plurality of polynucleotide samples comprises three or more token sequences attached thereto.

14. The composition of claim 1, wherein the two or more token sequences are not adjacent to one another.

15. The composition of claim 1, wherein the non-overlapping segments are restriction enzyme fragments.

16. The composition of claim 1, wherein the non-overlapping segments are amplicons.

\* \* \* \* \*

SEQUENCE LISTING

```
<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
```

```
                               -continued
<222> LOCATION: 1, 2, 3, 4, 5, 6, 7, 8, 9, 10, 11, 17, 18, 19, 20, 21,
      22, 23, 24
<223> OTHER INFORMATION: n = A,T,C or G

<400> SEQUENCE: 1
nnnnnnnnnn ngcagcnnnn nnnnccgc                                     28

<210> SEQ ID NO 2
<211> LENGTH: 28
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 5, 6, 7, 8, 9, 10, 11, 12, 18, 19, 20, 21, 22, 23, 24,
      25, 26, 27, 28
<223> OTHER INFORMATION: n = A,T,C or G

<400> SEQUENCE: 2
gcggnnnnnn nngctgcnnn nnnnnnnn                                     28

<210> SEQ ID NO 3
<211> LENGTH: 28
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 5, 6, 7, 8, 9, 15, 16, 17, 18, 19, 20, 21, 22, 23, 24,
      25, 26, 27, 28
<223> OTHER INFORMATION: n = A,T,C or G

<400> SEQUENCE: 3
ccgcnnnnng atgcnnnnnn nnnnnnnn                                     28

<210> SEQ ID NO 4
<211> LENGTH: 28
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 1, 2, 3, 4, 5, 6, 7, 8, 9, 10, 11, 12, 13, 14, 20, 21,
      22, 23, 24
<223> OTHER INFORMATION: n = A,T,C or G

<400> SEQUENCE: 4
nnnnnnnnnn nnnncgtagn nnnngcgg                                     28
```